United States Patent
Olwin et al.

(10) Patent No.: US 6,800,286 B1
(45) Date of Patent: Oct. 5, 2004

(54) CHIMERIC FIBROBLAST GROWTH FACTOR PROTEINS, NUCLEIC ACID MOLECULES, AND USES THEREOF

(75) Inventors: Bradley B. Olwin, Boulder, CO (US); Richard Scott Rosenthal, Raleigh, NC (US)

(73) Assignee: The Regents of the University of Colorado, Boulder, CO (US)

(*) Notice: Subject to any disclaimer, the term of this patent is extended or adjusted under 35 U.S.C. 154(b) by 0 days.

(21) Appl. No.: 09/377,675

(22) Filed: Aug. 19, 1999

Related U.S. Application Data

(60) Provisional application No. 60/097,160, filed on Aug. 19, 1998.

(51) Int. Cl.[7] .................. A61K 39/00; A61K 38/18; A61K 38/24; C07K 1/00
(52) U.S. Cl. ............... 424/185.1; 424/192.1; 514/2; 514/12; 530/350; 530/399
(58) Field of Search ............... 530/350, 399; 514/2, 12, 44; 424/192.1, 185.1

(56) References Cited

U.S. PATENT DOCUMENTS

| | | | |
|---|---|---|---|
| 5,604,293 A | 2/1997 | Fiddes et al. | 530/399 |
| 5,804,604 A | 9/1998 | Frankel et al. | 530/324 |
| 5,888,762 A | 3/1999 | Joliot et al. | 435/69.1 |

FOREIGN PATENT DOCUMENTS

| | | |
|---|---|---|
| WO | WO 91/18981 | 12/1991 |
| WO | WO 97/12912 | 4/1997 |

OTHER PUBLICATIONS

Derossi et al., *J. Biol. Chem.*, 269:10444–10450 (1994).
Femig et al., *Progress in Growth Factor Research*, 5:353–377 (1994).
Perez et al., *J. Cell Sci.*, 102:717–722 (1992).

*Primary Examiner*—John Ulm
*Assistant Examiner*—Olga N. Chernyshev
(74) *Attorney, Agent, or Firm*—Sheridan Ross, P.C.

(57) ABSTRACT

A chimeric fibroblast growth factor protein and recombinant nucleic acid molecule encoding the same are disclosed. The chimeric fibroblast growth factor protein is characterized by: fibroblast growth factor biological activity in the absence of heparan sulfate and, entry into a living cell in the absence of a receptor that binds to FGF. Also disclosed are a method of making the chimeric fibroblast growth factor protein and methods of using the chimeric fibroblast growth factor protein to promote fibroblast growth factor activity in a cell and to enhance a biological process associated with fibroblast growth factor activity.

15 Claims, 15 Drawing Sheets

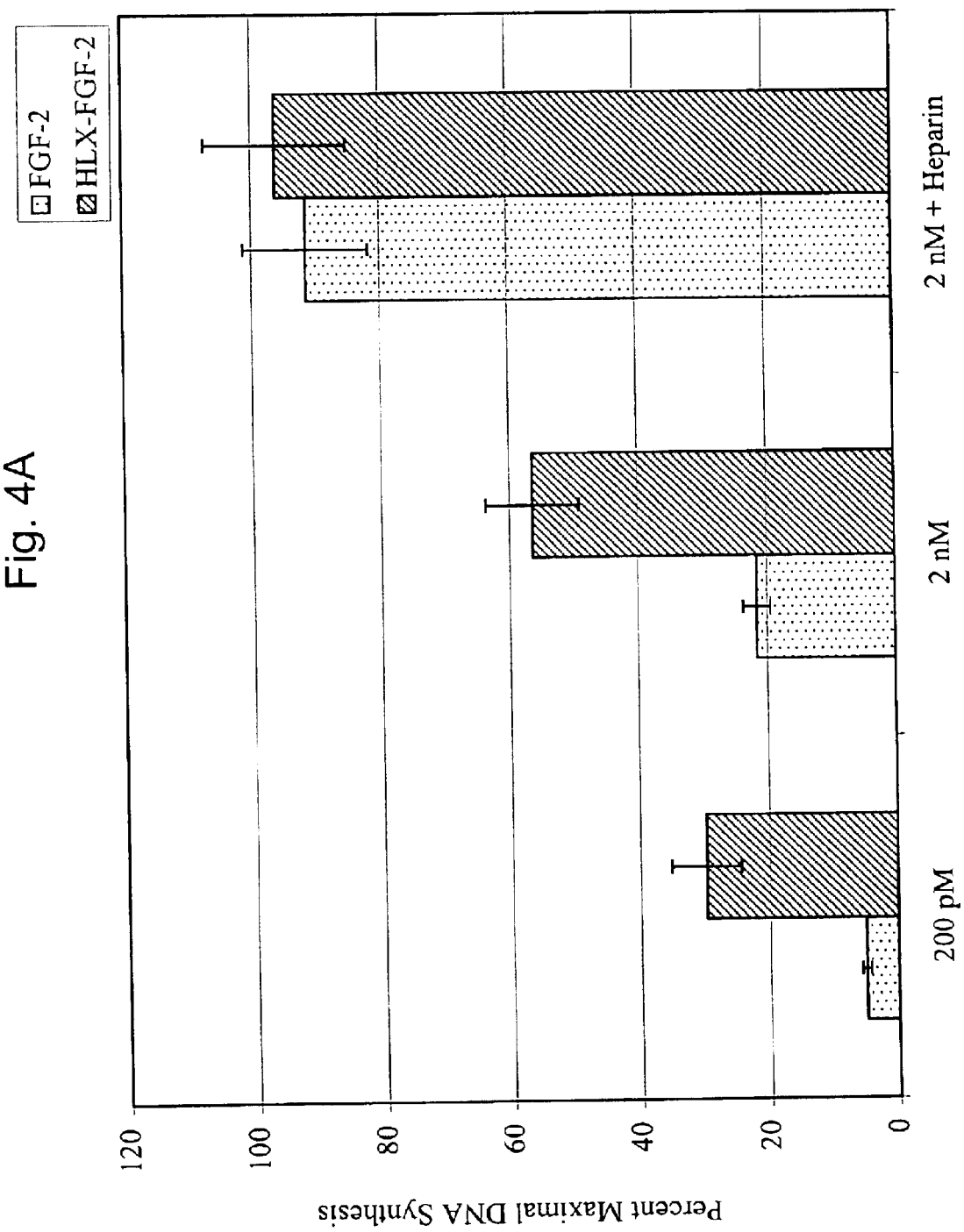

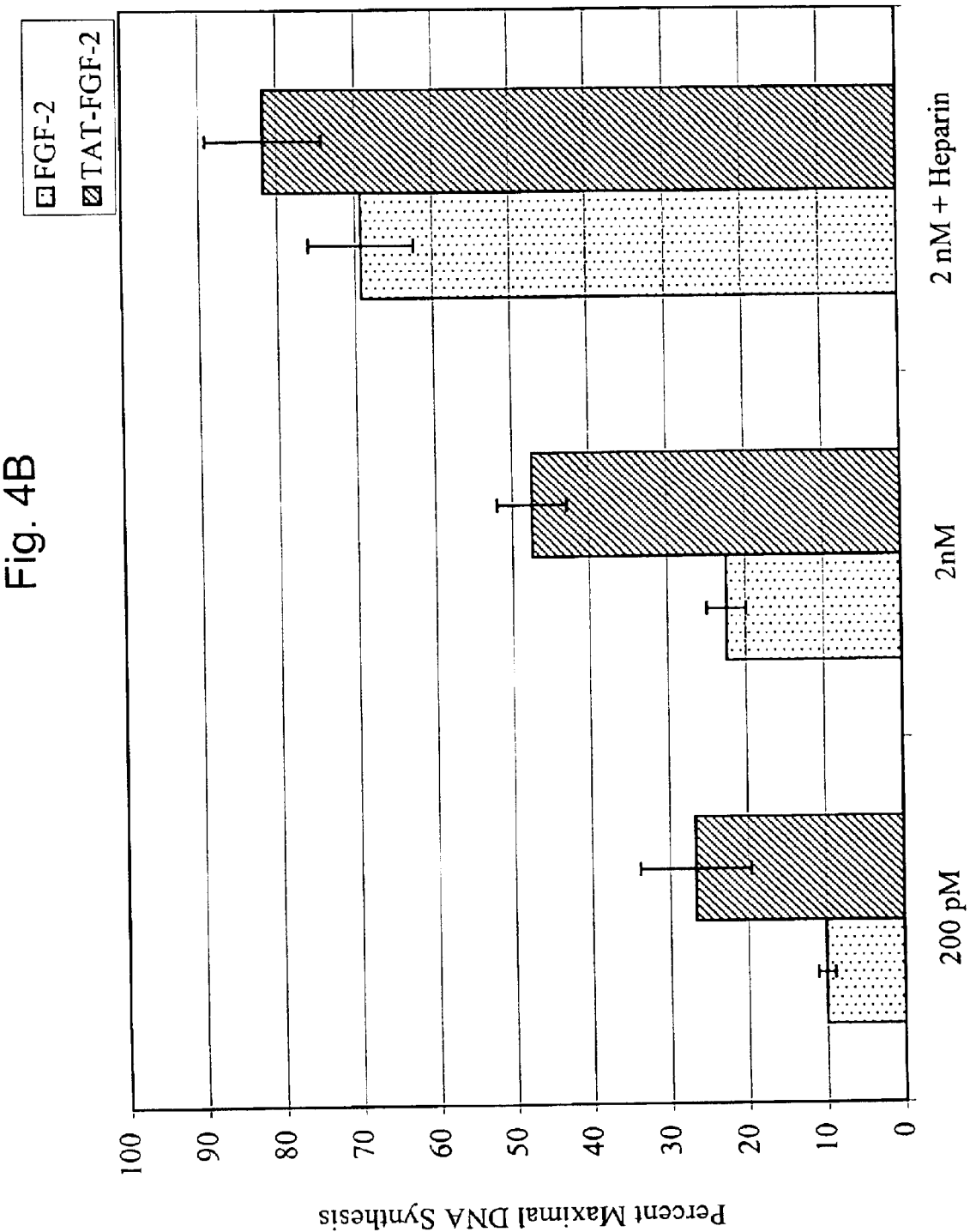

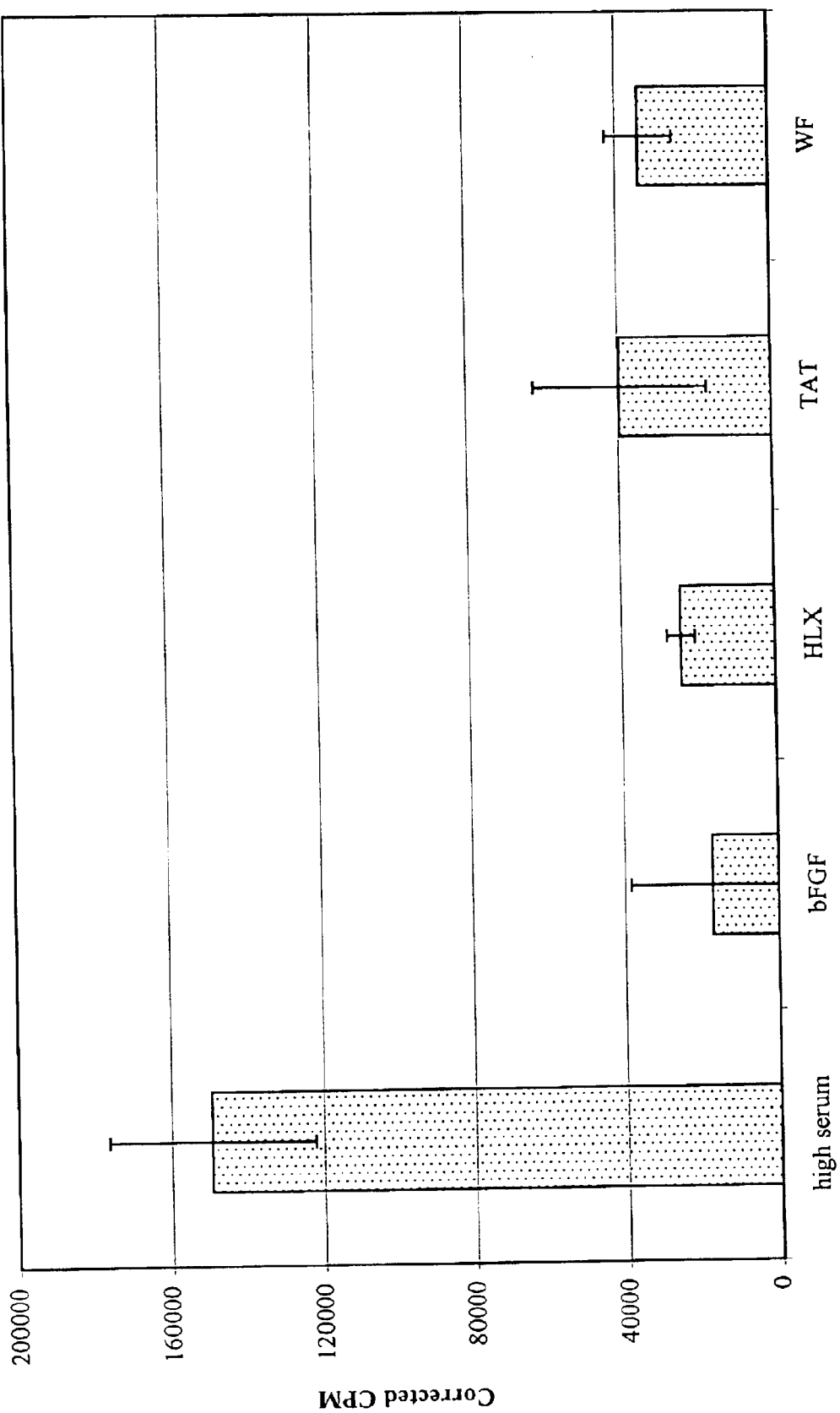

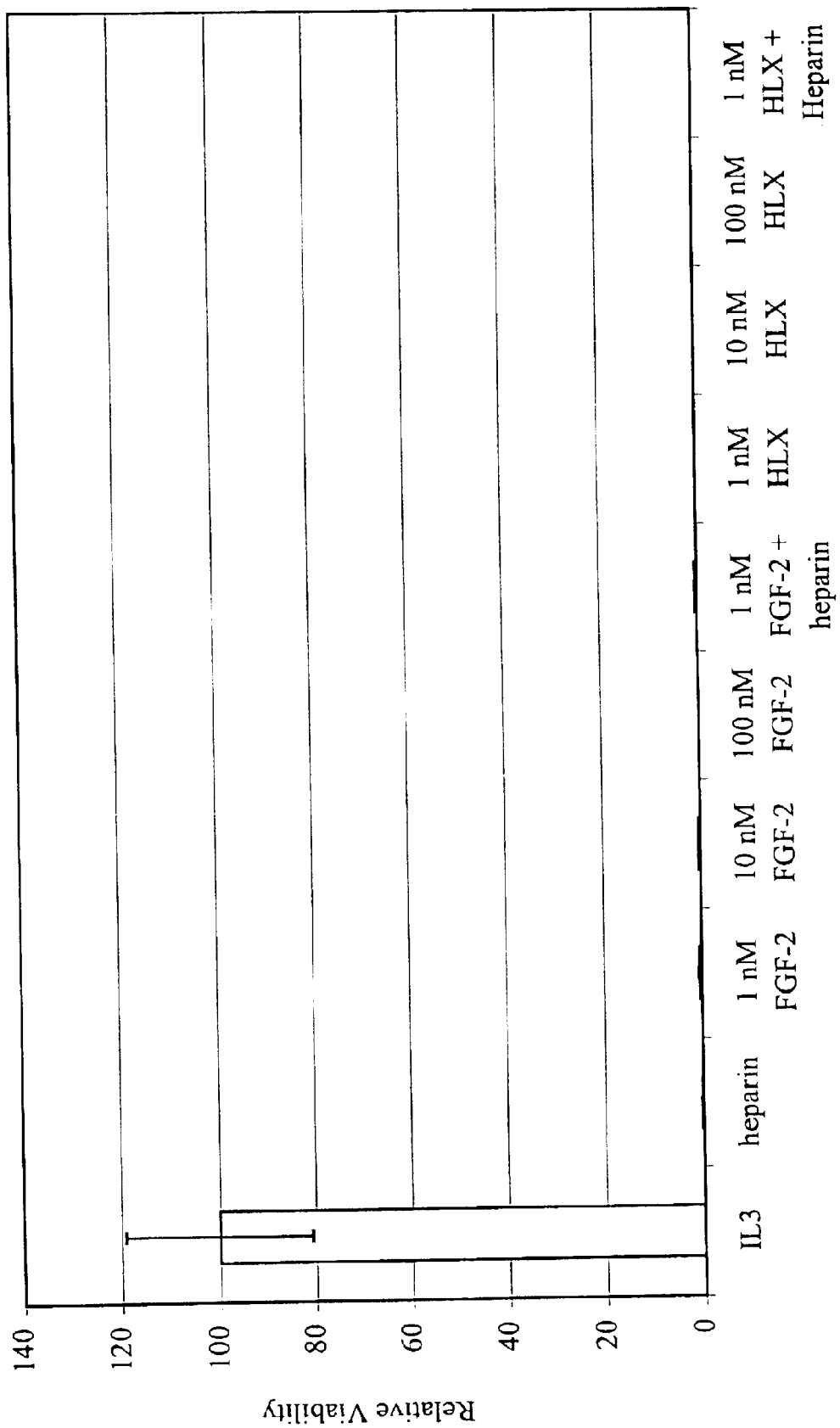

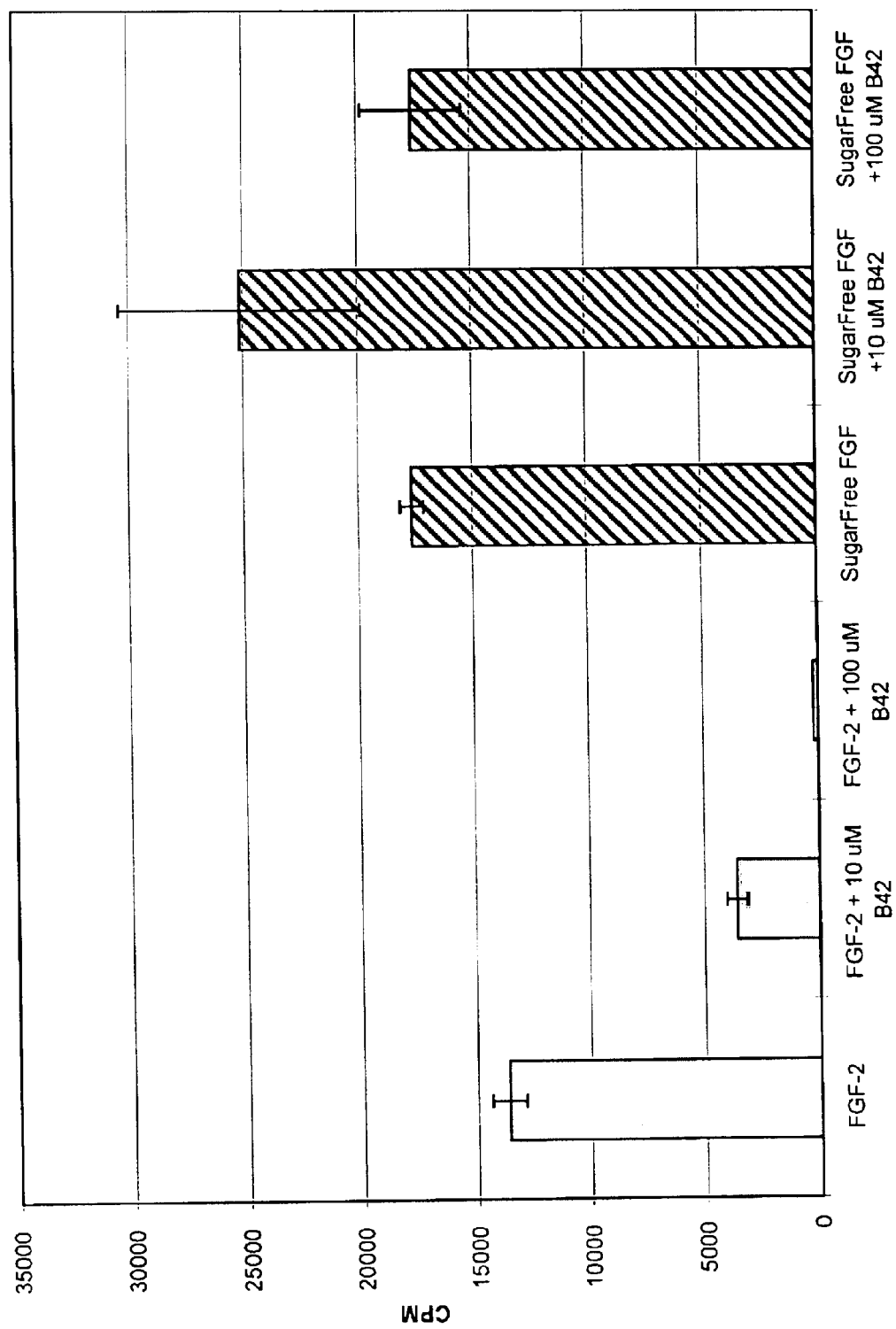

US 6,800,286 B1

CHIMERIC FIBROBLAST GROWTH FACTOR PROTEINS, NUCLEIC ACID MOLECULES, AND USES THEREOF

CROSS-REFERENCE TO RELATED APPLICATIONS

This application claims priority under 35 U.S.C. § 119(e) from U.S. Provisional Application Ser. No. 60/097,160, filed Aug. 19, 1998, entitled "Sugar Free FGF". The entire disclosure of U.S. Provisional Application Ser. No. 60/097,160 is incorporated herein by reference.

GOVERNMENT SUPPORT

This invention was made in part with government support under NIH Grant AR39467 and NIH Grant HL07851, each awarded by the National Institutes of Health. The government has certain rights to this invention.

FIELD OF THE INVENTION

The present invention generally relates to a chimeric fibroblast growth factor protein, and in particular, to a chimeric fibroblast growth factor protein which does not have an absolute requirement for heparan sulfate for biological activity. The present invention also relates to nucleic acid molecules encoding such a protein, and to therapeutic methods of using such a protein.

BACKGROUND OF THE INVENTION

Fibroblast growth factors (FGFs) comprise a growing family of proteins found throughout various organs and tissues of both developing and adult mammals. FGFs have been shown to mediate or influence numerous biological processes including mitogenesis, angiogenesis, wound healing, and neurogenesis, as well as limb patterning and outgrowth. Two particularly well known members of the FGF family include FGF-1 and FGF-2, also referred to as acidic FGF and basic FGF, respectively.

FGF-2, also referred to as basic fibroblast growth factor (bFGF), was one of the first FGFs to be identified and has been extensively studied. FGF-2 has been shown to be able to elicit various biological responses by binding to and activating specific cell-surface receptors called FGF receptor tyrosine kinases. In addition to the FGF receptor tyrosine kinase, it is generally agreed that heparan sulfate proteoglycans (or its soluble analog heparin) are necessary for both the FGF/FGF receptor interaction and the resulting biological activity. A relatively small number of studies have implicated the FGF ligand to have a role in mediating the biological activity of these factors, yet the mechanism by which this occurs remains poorly understood.

The commonly accepted paradigm for growth factor mediated activation of receptor tyrosine kinases depicts ligand-facilitated multimerization and trans-phosphorylation of the cognate receptor resulting in the recruitment of intracellular adapter and signal-transducing molecules. A complex cascade of intracellular signaling events terminating in the nucleus is thought to dictate the resulting biological response(s) (Fantl, et al., (1993) *Ann. Rev. Biochem.*, 62:453–81; Klint, et al., (1999) *Frontiers in Bioscience*4: D165–77). Concomitantly, the ligand is internalized and subjected to degradation or other alternative fates (Cuatrecasas, (1982) Epidermal growth factor: uptake and fate. Ciba Foundation Symposium, 96–108; Lewis, et al., (1996)*Exp. Eye Res.*, 62:309–24; Massagu, etal., (1986) *J. Cell. Phys.*, 128:216–22; Naka, et al., (1993) *Febs Letters*, 329:147–52; Sorkin, et al., (1988) *Exp. Cell Res.*, 175:192–205). However, mounting evidence for a number of growth factors and cytokines (FGF, nerve growth factor, PDGF, Schwannoma-derived growth factor, insulin, angiotensin 11 and growth hormone) suggest that they may act intracellularly and in many cases support a site of action for these factors in the nucleus (Jans, et al., (1998) *Bioessays*, 20:400–11; Prochiantz, et al., (1995) *Bioessays*, 17:39–44; Imamura, et al., (1990) *Science*, 249:1567–1570; Kimura, H. (1993) *Proc. Natl Acad. Sci. USA*, 90:2165–9). This has been extensively documented for the FGF family (Imamura, et al., (1990) *Science*, 249:1567–1570; Baldin, et al., (1990) *EMBO J.*, 9:1511–1517; Imamura, et al., (1994) *Exp. Cell Res.*, 215:363–372). However, the only specific activity described for FGF in the nucleus is enhancement of ribosomal RNA synthesis (Bouche, et al., (1987) *Proc. Natl. Acad. Sci. USA*, 84:6770–6774). This activity was also correlated with the ability of FGF-2 to bind to and regulate the activity of protein kinase CK2 which has been shown to act directly on nucleolin, a nucleolar protein involved in the control of rDNA transcription (Bonnet, et al., (1996) *J. Biol. Chem.*, 271:24781–7). Additionally, a number of studies have shown that translocation of FGF-2 or FGF-1 to the nucleus either in the absence or presence of their cognate receptors is involved in DNA synthesis, but specific FGF targets have not been identified (Hawker, et al., (1994) *Am. J. Phys.*, 266:H107–20; Hawker, et al., (1994) *In Vitro Cellular And Developmental Biology. Animal*30A:653–63; Wiedlocha, et al. (1996) *Mol. Cell. Biol*, 16:270–280; Wiedlocha, et al., (1994) *Cell*, 76:1039–1051). FGF-1 and FGF-2 ligands have been detected in intracellular compartments. Both ligands have been proposed to have specific intracellular sites of action that include stimulation of DNA synthesis for FGF-1 and stimulation of ribosomal gene transcription for FGF-2. A receptor-independent role for FGF-1 has been proposed using an FGF-1-Diphtheria toxin conjugate, which allowed receptor-independent, cytoplasmic entry of FGF-1.

The evidence for the activity of FGF proteins in a variety of beneficial biological processes, combined with the evidence indicating an intracellular site of action and a potential direct role for FGF proteins in signal transduction affecting cell proliferation and differentiation, make FGF proteins a desirable candidate molecule for the development of modified proteins as regulators of cell growth and differentiation, for the use in applications such as promoting wound healing, treating myocardial infarction (Svet-Moldavsky, G. J., et al, Lancet (Apr. 23, 1977) 913; U.S. Pat. Nos. 4,296,100 and 4,378,347), treating degenerative neurological disorders, such as Alzheimer's disease and Parkinson's disease (Walicke, P., et al, *Proc Natl Acad Sci* (USA) (1986) 83:3012–3016), promoting angiogenesis, promoting bone healing, and promoting muscle healing. Therefore, there is a need in the art for modified FGF proteins having FGF biological activity and novel attributes which improve their suitability for use in therapeutic protocols.

SUMMARY OF THE INVENTION

The present invention generally relates to a chimeric fibroblast growth factor (FGF) protein characterized by: (a) fibroblast growth factor biological activity in the absence of heparan sulfate; and, (b) an ability to enter a living cell in the absence of a receptor that binds to FGF. The present invention also relates to recombinant nucleic acid molecules encoding such a chimeric FGF protein, to therapeutic compositions including such a chimeric FGF protein, and to methods of making and using such a chimeric FGF protein.

One embodiment of the present invention is a chimeric fibroblast growth factor (FGF) which includes: (a) a biologically active fibroblast growth factor (FGF) protein having a first amino acid sequence; and, (b) a penetratin peptide having a second amino acid sequence. The penetratin peptide transports the chimeric fibroblast growth factor (FGF) across a lipid bilayer of a cell independently of the presence of an FGF receptor, and the second amino acid sequence is linked to the first amino acid sequence. The chimeric fibroblast growth factor (FGF) is characterized by: (i) fibroblast growth factor (FGF) biological activity in the absence of heparan sulfate; and, (ii) entry into a living cell in the absence of a receptor that binds to FGF. In one embodiment, the FGF biological activity of(i) is characterized by: (a) repression of terminal differentiation in the absence of heparan sulfate; and/or, (b) promotion of cell proliferation in the absence of heparan sulfate. In a preferred embodiment, the second amino acid sequence is linked to the N-terminus of the first amino acid sequence.

In the chimeric FGF of the present invention, the FGF protein is encoded by a nucleic acid molecule that hybridizes under stringent hybridization conditions to a nucleic acid molecule encoding any naturally occurring FGF protein, with an FGF protein selected from the group consisting of fibroblast growth factor-1 (FGF-1) protein and fibroblast growth factor-2 (FGF-2) protein being preferred. The FGF protein encoded by the nucleic acid molecule has FGF biological activity. In a preferred embodiment, the FGF protein is selected from the group consisting of a fibroblast growth factor-1 (FGF-1) protein and a fibroblast growth factor-2 (FGF-2) protein. Other preferred FGF proteins include, but are not limited to: FGF proteins having an amino acid sequence selected from the group of SEQ ID NO:5, SEQ ID NO:6, SEQ ID NO:7 and SEQ ID NO:8. A preferred FGF protein for use in the chimera of the present invention is a fibroblast growth factor-2 protein. In one embodiment, the FGF protein has an amino acid sequence comprising from position 18 through position 172 of SEQ ID NO:2 (HLX-FGF-2) or from position 17 through 171 of SEQ ID NO:4 (TAT-FGF-2). Preferably, a biologically active FGF protein useful in a chimera of the present invention is encoded by a nucleic acid sequence comprising from nucleotide 59 to 523 of SEQ ID NO:1 (HLX-FGF-2) or from nucleotide 59 to 523 of SEQ ID NO:3.

In one embodiment, the penetratin peptide portion of a chimeric FGF of the present invention can include: (a) a first peptide having an amino acid sequence selected from the group consisting of:

(i) $X_1$-$X_2$-$X_3$-$X_4$-$X_5$-$X_6$-$X_7$-$X_8$-$X9$-$X_{10}$-$X_{11}$-$X_{12}$-$X_{13}$-$X_{14}$-$X_{15}$-$X_{16}$; and, (ii) $X_{16}$-$X_{15}$-$X_{14}$-$X_{13}$-$X_{12}$-$X_{11}$-$X_{10}$-$X_9$-$X_8$-$X_7$-$X_6$-$X_5$-$X_4$-$X_3$-$X_2$-$X_1$;

wherein $X_1$, $X_2$, $X_3$, $X_4$, $X_5$, $X_7$, $X_8$, $X_9$, $X_{10}$, $X_{11}$, $X_{12}$, $X_{13}$, $X_{14}$, $X_{15}$, and $X_{16}$ each represent an α-amino acid, between 6 and 10 of which are hydrophobic amino acids; and wherein $X_6$ represents Trp; and, (b) a second peptide comprising amino acid residues 49–57 of HIV Tat protein (SEQ ID NO:17). In a preferred embodiment, the second peptide of (b) does not comprise amino acid residues 22–36 or 73–86 of HIV Tat protein (SEQ ID NO:17).

The first penetratin peptide can include a peptide comprising helix 3 of a homeobox domain and a homeobox domain, and fragments and homologues thereof Such peptides comprise an amino acid sequence including, but are not limited to: SEQ ID NO:9, amino acid residues 42 through 58 of SEQ ID NO:9, amino acid residues 43 through 59 of SEQ ID NO:9, amino acid residues 43 through 58 of SEQ ID NO:9, amino acid residues 58 through 43 of SEQ ID NO:9, SEQ ID NO:10, SEQ ID NO:11, SEQ ID NO:12, SEQ ID NO:13, SEQ ID NO:14, SEQ ID NO:15, and/or SEQ ID NO:16. In one embodiment, such a peptide comprises amino acid residues 2–17 of SEQ ID NO:2. Preferably, such a peptide is encoded by a nucleic acid sequence comprising nucleotides 11 to 58 of SEQ ID NO:1.

The second penetratin peptide can include an HIV Tat protein or fragments or homologues thereof. Preferred peptides comprise an amino acid sequence that includes, but is not limited to: amino acid residues 37–72 of SEQ ID NO:17, amino acid residues 38–72 of SEQ ID NO:17, amino acid residues 47–72 of SEQ ID NO:17, amino acid residues 37–58 of SEQ ID NO:17, amino acid residues 38–58 of SEQ ID NO:17, amino acid residues 47–58 of SEQ ID NO:17, amino acid residues 1–21 and 38–72 of SEQ ID NO:17, amino acid residues 47–62 of SEQ ID NO:17, amino acid residues 38–62 of SEQ ID NO:17, amino acid residues 1–72 of SEQ ID NO:17, amino acid residues 1–58 of SEQ ID NO:17, and/or amino acid residues 48–60 of SEQ ID NO:17. In one embodiment, such a peptide comprises amino acid residues 48–60 of SEQ ID NO:17 or amino acid residues 2–14 of SEQ ID NO:4. Preferably, such a peptide is encoded by a nucleic acid sequence comprising residues 14 to 52 of SEQ ID NO:3.

A chimeric fibroblast growth factor (FGF) of the present invention includes a chimera comprising an amino acid sequence selected from the group consisting of SEQ ID NO:2 (HLX-FGF-2) and SEQ ID NO:4 (TAT-FGF-2). Preferably, such a chimeric FGF is encoded by a recombinant nucleic acid molecule having a nucleic acid sequence of SEQ ID NO:1 and SEQ ID NO:3, respectively.

Another embodiment of the present invention relates to a therapeutic composition comprising the chimeric fibroblast growth factor (FGF) of the present invention and a pharmaceutically acceptable excipient.

Yet another embodiment of the present invention relates to a recombinant nucleic acid molecule encoding a chimeric fibroblast growth factor (FGF) of the present invention as described above. Such a recombinant nucleic acid molecule comprises: (a) a first isolated nucleic acid sequence encoding a biologically active fibroblast growth factor (FGF) protein; and, (b) a second isolated nucleic acid sequence encoding a penetratin peptide that transports the chimeric fibroblast growth factor (FGF) across a lipid bilayer of a cell independently of the presence of an FGF receptor, wherein the second nucleic acid sequence is linked to the first nucleic acid sequence. The first and second nucleic acid sequences are operatively linked to a transcription control sequence. Such a chimeric fibroblast growth factor (FGF) is characterized by: (i) fibroblast growth factor biological activity in the absence of heparan sulfate; and, (ii) entry into a living cell in the absence of a receptor that binds to FGF. Preferred chimeric FGF proteins encoded by a recombinant nucleic acid molecule of the present invention are described above.

Another embodiment of the present invention relates to a recombinant cell that expresses the recombinant nucleic acid molecule of the present invention described above. Another embodiment of the present invention is a recombinant virus that comprises the recombinant nucleic acid molecule of the present invention.

Yet another embodiment of the present invention relates to a method to produce a chimeric fibroblast growth factor (FGF), comprising culturing in an effective medium a recombinant cell comprising a recombinant nucleic acid molecule encoding a chimeric fibroblast growth factor protein as described above.

Another embodiment of the present invention relates to a method to promote fibroblast growth factor biological activity in a cell and particularly, to repress terminal differentiation and promote proliferation in a cell. Such a method includes the steps of administering to a cell a chimeric fibroblast growth factor (FGF) protein of the present invention as described above. In one embodiment, the cell has reduced heparan sulfate proteoglycan production characterized by a reduction in both repression of terminal differentiation and promotion of proliferation in the presence of naturally occurring fibroblast growth factor. In another embodiment, the cell is a cell of patient that has a condition selected from the group consisting of stroke, nerve damage, bone damage, muscle damage, and a wound. Such a chimeric FGF can be administered by any route, including in vitro, in vivo, and ex vivo.

Another embodiment of the present invention relates to a method to enhance a biological process selected from the group consisting of mitogenesis, angiogenesis, wound healing, neurogenesis, limb patterning, limb outgrowth, comprising administering to cells associated with the biological process a chimeric fibroblast growth factor (FGF) of the present invention as described above.

BRIEF DESCRIPTION OF THE DRAWINGS

FIG. 4A is a graph demonstrating that HLX-FGF-2 chimeric protein has an attenuated requirement for heparan sulfate.

FIG. 4B is a graph demonstrating that TAT-FGF-2 chimeric protein has an attenuated requirement for heparan sulfate.

FIG. 5A is a graph showing that chimeric FGF-2 requires an FGF receptor in order to function in L6AI (FR-) cells.

FIG. 5B is a graph showing that chimeric FGF-2 requires an FGF receptor in order to function in BaF3 lymphoid cells.

FIG. 7B is a graph showing that in MM14 cells treated with Tyrphostin B42, growth is substantially inhibited in cells treated with FGF-2, but not in cells treated with HLX-FGF-2.

DETAILED DESCRIPTION OF THE INVENTION

Figure 1:
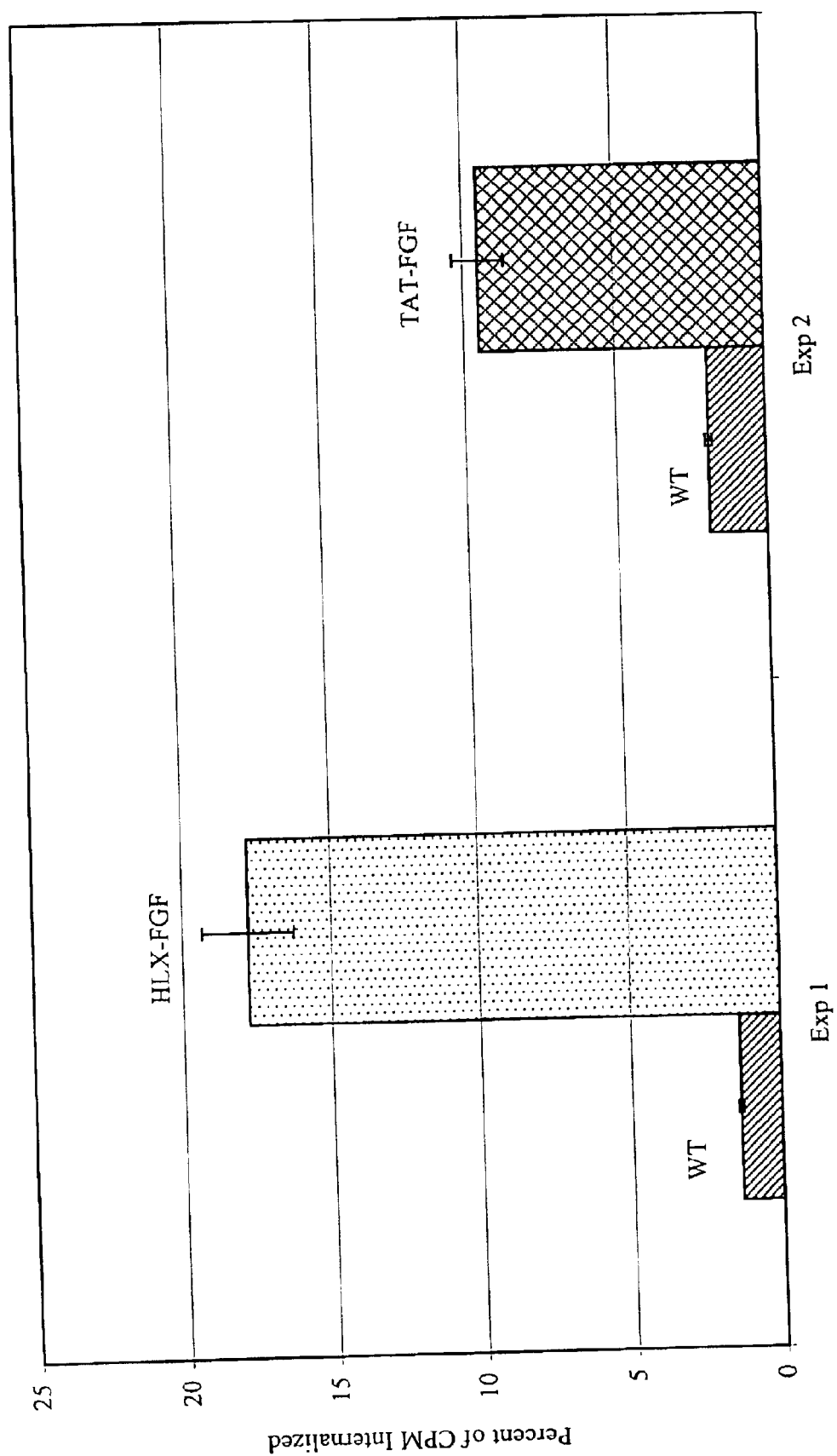
FIG. 1 is a graph showing that chimeric FGF-2 molecules are capable of crossing the plasma membrane independent of receptor-mediation.

The present invention generally relates to a chimeric fibroblast growth factor (FGF) protein characterized by: (a) fibroblast growth factor biological activity in the absence of heparan sulfate; and, (b) an ability to enter a living cell in the absence of a receptor that binds to FGF. The present invention also relates to recombinant nucleic acid molecules encoding such a chimeric FGF protein, to therapeutic compositions including such a chimeric FGF protein, and to methods of making and using such a chimeric FGF protein.

The present inventors describe herein the development of a novel cell-permeant FGF chimera, also referred to herein as a penetratin-FGF chimera or penetratin-FGF fusion protein (described in detail below), that is capable of acting intracellularly to mediate FGF biological activity, such as repression of differentiation and/or stimulation of proliferation in a cell. Surprisingly, the inventors have discovered that, although the penetratin-FGF chimera of the present invention has biological activity substantially similar to a naturally occurring FGF, the biological activity of the penetratin-FGF chimera does not demonstrate the absolute heparan sulfate-dependency seen for wild type FGFs. Furthermore, the chimeric penetratin-FGF molecule facilitated cell proliferation even when the ligand binding domain of the cell surface receptors was removed by proteolysis. Unexpectedly, the present inventors have also found that the intracellular activity of the penetratin-FGF chimera is completely dependent on the expression of FGF receptors.

More particularly, the present inventors have designed and constructed chimeric proteins which include FGF proteins fused to short peptide sequences which are referred to collectively herein as "penetratins", which have been shown to be capable of shuttling various cargo molecules across the plasma membrane (See for example U.S. Pat. No. 5,888, 762, 1999 to Joliot et al., PCT Publication No. WO 91/18981 to Centre National de la Recherche Scientifique, PCT Publication No. WO 97/12912 to Centre National de la Recherche Scientifique, U.S. Pat. No. 5,804,604,1998) to Frankel et al., Perez et al., 1992, *J. Cell Sci.* 102;717–722, Derossi et al., 1994, *J. Biol. Chem*, 269:10444–10450, Bloch-Gallego, et al., (1993) *J. Cell Biol.* 120:485–92; Joliot, et al., (1991) *Proc. Nat'l Acad. Sci. USA*, 88:1864–8; Le Roux, et al., (1993) *Proc. Nat'l Acad. Sci. USA*, 90:9120–4; Mann, et al. (1991) *Embo Journal*, 10:1733–9; Vives, et al., (1997) *J. Biol. Chem.*, 272:16010–7; Viv s, et al., (1994) *J. Virol.*, 68:3343–53, each of which is incorporated herein by reference in its entirety). Specifically, two chimeric FGF-2 proteins containing either a portion of the Drosophila Antenapedia protein (HLX-FGF-2) or the HIV Tat protein (TAT-FGF-2) were constructed (see Examples, Table 2). The initial utility of these chimeric molecules lies in their ability to enter a cell independent of receptor-mediated or other common endocytic pathways as is evidenced by the capacity of the chimeric proteins to facilitate internalization at 4° C. Indeed, both the TAT- and HLX-FGF-2 fusion proteins are capable of entering cells that do not possess detectable cell surface FGFRs and that fail to respond to FGF in an FGFR dependent manner. Moreover, cellular entry by these fusion molecules was efficient at 4° C., consistent with penetratin-mediated internalization. It is noted that one advantage of a chimeric FGF protein of the present invention is that it is capable of penetrating not only the plasma membrane of a cell in the absence of binding to a receptor, but it is also capable of permeating any membrane within a cell (e.g., to enter the nucleus), and therefore, it's entry into an intracellular compartment is not constrained within a cell. The FGF-2 fusions were also indistinguishable from wild type FGF-2 in their biological activity and receptor binding. Both wild type and penetratin FGF-2 proteins required heparan sulfate to bind efficiently to fibroblast growth factor receptor 1 (FGFR1) present on MM14 cells.

Surprisingly, however, the present inventors discovered that the chimeric FGF-penetratin proteins had unexpected properties which distinguished them from naturally occurring FGF proteins and from any other previously described modified FGF proteins. More particularly, the present inventors discovered that the biological activity of HLX-FGF-2 and TAT-FGF-2 was not absolutely dependent on heparan sulfate. Both penatratin-FGF-2 fusion proteins were active in the absence of heparin in cells treated with chlorate. Additionally, FGFR1 expressing BaF3 cells, which do not express heparan sulfate proteoglycans, responded to HLX-FGF-2 treatment even in the absence of heparin. Control experiments with the isolated HLX penetratin peptide failed to elicit any detectable response in either MM14 or BaF3 cells (data not shown). As such, it is unlikely that the heparin-independent activity demonstrated by the FGF-2 fusion proteins is due to the presence of the penetratin sequence. Thus, these experiments indicated a disparity between the binding of penetratin-FGF-2 fusions to cell surface FGFR1, which requires heparan sulfate, and the ability of the fusions to promote proliferation in MM14 cells or survival in BaF3 cells. The present inventors additionally discovered that surprisingly, the intracellular activity of the penetratin-FGF chimera was completely dependent on the expression of FGF receptors, that inactivation of the FGFR1 tyrosine kinase is necessary for the biological activity of the penetratin-FGF chimeras of the present invention, and that activation of the raf/ERK pathway appears to be required for the biological activity of the penetratin-FGF chimeras.

In addition to a plethora of therapeutic uses for the penetratin-FGF chimeras that encompass current uses for wildtype FGF (e.g., wound healing, neurogenesis, etc.) the properties of the novel chimeric FGF protein described herein suggest potential therapeutic roles for penetratin-FGF chimeras in pathological conditions where normal FGF function does not occur due to biochemical defects in the normal FGF signaling pathways. For example, it is known that genetic defects in FGF receptors are responsible for most forms of dwarfism, and therefore, a chimeric FGF of the present invention, which does not require binding to an FGF receptor for entry into a cell, are believed to be extremely valuable as a therapeutic composition for the treatment of dwarfism. Additionally, it has been shown that the biological function of heparan sulfate with regard to FGF activity can be either inhibitory or stimulatory, depending on the cell type and the FGF receptor type. The relative heparan sulfate independence of a chimeric FGF of the present invention can therefore be used advantageously in that an FGF receptor could be activated in a cell where the FGFR is not normally activated due to inhibitory action of heparan sulfate, and vice versa. In other words, the ability to bypass the regulatory function of heparan sulfate on FGF receptors can be used advantageously in therapeutic protocols depending on the desired result. Other pathological conditions may also be responsive to FGF therapy (e.g., at the time of filing, wild-type FGF-2 is in clinical trials for the treatment of stroke) even though specific defects in FGF signaling do not exist. One current hypothesis regarding FGF receptors is that they are tightly regulated and not easily activated. Therefore, penetratin-FGF chimeras of the present invention are believed to be able to potentiate therapeutic effects by stimulating cells which are normally recalcitrant to FGF treatment and therefore be more effective than wildtype FGF.

One embodiment of the present invention relates to a chimeric fibroblast growth factor (FGF), comprising: (a) a biologically active fibroblast growth factor (FGF) protein having a first amino acid sequence; and, (b) a penetratin peptide having a second amino acid sequence, the second amino acid sequence being linked to the first amino acid sequence. The penetratin peptide transports the chimeric fibroblast growth factor (FGF) across a lipid bilayer of a cell independently of the presence of an FGF receptor. It is noted that the penetratin peptide can transport the chimeric fibroblast growth factor across any cellular membrane, and is not limited to transport across the plasma membrane. The chimeric fibroblast growth factor (FGF) is characterized by: (i) fibroblast growth factor biological activity in the absence of heparan sulfate; and, (ii) an ability to enter a living cell in the absence of a receptor that binds to FGF. In one embodiment, fibroblast growth factor biological activity can include: (a) an ability to repress terminal differentiation in the absence of heparan sulfate; and (b) an ability to promote cell proliferation in the absence of heparan sulfate. Other biological activities of FGF are described below.

According to the present invention, the terms "chimera" or "chimeric" with regard to a protein refer to a protein that is composed of amino acid sequences derived from at least two distinct sources (i.e., at least two heterologous amino acid sequences). As used herein, a chimeric protein is not a single naturally occurring protein, but rather, has been synthesized or genetically engineered. One type of chimeric protein is known in the art as a fusion protein. According to the present invention, the phrases "chimeric fibroblast growth factor protein" and "penetratin-FGF chimera" or "penetratin-FGF protein" are used to refer to the same chimeric protein of the present invention, and thus can be used interchangeably.

According to the present invention, a chimeric fibroblast growth factor (FGF) protein is characterized as having fibroblast growth factor biological activity in the absence of heparan sulfate. Fibroblast growth factor biological activity is defined herein a measurable activity that is indicative of the biological activity of a naturally occurring fibroblast growth factor protein, as measured by an in vitro or in vivo assay. Such biological activities include, but are not limited to: an ability to promote cell proliferation (e.g., in a cell line such as MM14 as described in the Examples), an ability to repress terminal differentiation in a cell (e.g., in a cell line such as MM14 described in the Examples or bovine brain capillary endothelial cells), an ability to promote angiogenesis in vivo in a chicken chorioallantoic membrane assay, promotion of wound healing in vivo, promotion of osteogenesis on osteoblasts in an in vivo or in vitro assay, promotion of nerve outgrowth (primary neurons or neuronal cell lines). In vitro and in vivo assays for measuring FGF biological activity are well known in the art. For example, such assays are described in Gospodarowicz et al., 1985, *J. Cell Physiol.* 122:323–332, Gospodarowicz, 1983, *J. Cell Physiol.* 97:1677–1685, Esch et al., 1985, *Proc. Nat. Acad. Sci.* (USA) 82:6507–6511, Gospodarowicz et al., 1986, *J. Cell Physiol.* 127:121–136, Davidson et al., 1985, *J.C.B.* 100:1219–1227, and the Examples section. It is noted that modified forms of FGF, such as the chimeric penetratin-FGF proteins described herein, may have different quantitative activity and specificity than a naturally occurring FGF protein, and such variations are intended to be encompassed by the present invention.

According to the present invention, FGF biological activity of a protein is evaluated separately from the protein's requirement for entry into a cell (e.g., by receptor or by other means) as well as from the protein's requirement for heparan sulfate or exogenously added heparin (e.g., a protein can have FGF biological activity in the absence of heparan sulfate or other exogenously added heparin and/or in the absence of entering a cell via an FGF receptor). In other words, the ability to enter a cell via an FGF receptor or a dependence on heparan sulfate for activity is not used as a measure of FGF biological activity according to the present invention. A particular advantage of a chimeric FGF protein of the present invention is that the protein possesses the unique property of "heparan sulfate independence" (i.e., no absolute requirement for heparan sulfate for biological activity), a feature which has not been reported for any of the at least 20 known FGF family members or for any previously described modified FGF. FGFs are known to mediate numerous biological responses in many different tissues. The effects of FGFs require both a receptor tyrosine kinase specific for FGFs as well as heparan sulfate proteoglycans (HSPGs; or an analog compound, heparin) to bring about a biological response. It has become increasingly clear that HSPGs are critically important to the biological activity of naturally occurring FGF (e.g., as both inhibitory and stimulatory factors). Therefore, the chimeric FGF proteins of the present invention will have potential therapeutic value for use in pathologic conditions manifested by the inability of "normal" FGFs to generate necessary biological signals due to aberrant or abnormal heparan sulfate proteoglycan production. Furthermore, HSPGs/heparin have been postulated to stabilize FGFs and protect them from extracellular proteolysis. The "heparan sulfate independence" demonstrated by the chimeric FGF proteins of the present invention also suggest that these proteins may be more resistant to degradation than the native FGF protein.

A chimeric fibroblast growth factor protein of the present invention also has the ability to enter a living cell in the absence of a receptor that binds to FGF. In other words, although a chimeric FGF protein of the present invention may be capable of binding to an FGF receptor and of entering a cell via internalization of the chimeric FGF/FGF receptor complex, a chimeric FGF protein of the present invention can also enter a cell or cross any cellular membrane independently of receptor-mediated or other common endocytic pathways, and independently of the temperature and energy requirements of most biological processes (e.g., a chimeric FGF protein can enter a cell at 4° C.).

One portion of a chimeric FGF protein of the present invention is a biologically active fibroblast growth factor protein. Accordingly, a biologically active FGF protein meets the requirements for FGF biological activity as discussed in detail above. Specifically, a biologically active FGF protein has a measurable activity or function that is indicative of the biological activity of a naturally occurring fibroblast growth factor protein, as measured by an in vitro or in vivo assay (described in detail above). According to the present invention, reference to a "fibroblast growth factor (FGF) protein" can include any full-length FGF protein, truncated FGF protein, or any homologue of such an FGF protein. According to the present invention, an FGF homologue includes proteins in which at least one or a few, but not limited to one or a few, amino acids of full-length FGF have been accidentally or deliberately deleted (e.g., a truncated version of the protein, such as a peptide), inserted, inverted, substituted and/or derivatized (e.g., by glycosylation, phosphorylation, acetylation, myristoylation, prenylation, palmitation, amidation and/or addition of glycosylphosphatidyl inositol), wherein the FGF homologue has FGF biological activity as described previously herein. An FGF protein homologue can be identified as a protein having at least one epitope which elicits an immune response against a naturally occurring FGF protein. In another embodiment, a homologue of an FGF protein is a protein having an amino acid sequence that is sufficiently similar to a naturally occurring FGF amino acid sequence that a nucleic acid sequence encoding the homologue is capable of hybridizing under stringent conditions to (i.e., with) a complement of a nucleic acid molecule encoding the naturally occurring FGF protein. A nucleic acid sequence complement of nucleic acid sequence encoding FGF refers to the nucleic acid sequence of the nucleic acid strand that is complementary to (i.e., can form a complete double helix with) the strand which encodes FGF. It will be appreciated that a double stranded DNA which encodes a given amino acid sequence comprises a single strand DNA and its complementary strand, such complementary strand having a sequence that is a complement to the single strand DNA. As such, nucleic acid molecules which encode an FGF protein of the present invention can be either double-stranded or single-stranded, and include those nucleic acid molecules that form stable hybrids under stringent hybridization conditions with a nucleic acid sequence that encodes the amino acid sequence of an FGF protein, and/or with the complement of the nucleic acid that encodes amino acid sequence of an FGF protein. Methods to deduce a complementary sequence are known to those skilled in the art. It should be noted that since amino acid sequencing and nucleic acid sequencing technologies are not entirely error-free, the sequences presented herein, at best, represent apparent sequences of FGF proteins included in the present invention.

As used herein, stringent hybridization conditions refer to standard hybridization as conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31–9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267–284; Meinkoth et al., ibid., is incorporated by reference herein in its entirety.

More particularly, stringent hybridization and washing conditions, as referred to herein, refer to conditions which permit isolation of nucleic acid molecules having at least about 70% nucleic acid sequence identity with the nucleic acid molecule being used to probe in the hybridization reaction, more particularly at least about 75%, and most particularly at least about 80%. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6× SSC (0.9 M Na$^+$) at a temperature of between about 20° C. and about 35° C., more preferably, between about 280° C. and about 40° C., and even more preferably, between about 35° C. and about 45° C. In particular embodiments, stringent hybridization conditions for DNA:RNA hybrids include hybridization at an ionic strength of 6× SSC (0.9 M Na$^+$) at a temperature of between about 30° C. and about 45° C., more preferably, between about 38° C. and about 50° C., and even more preferably, between about 45° C. and about 55° C. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 TO 9.62.

Preferably, nucleic acid molecules encoding biologically active FGF proteins suitable for use in a chimeric FGF protein of the present invention have at least about 70%, more preferably, at least about 80% and most preferably, at least about 90% identity with a nucleic acid sequence encoding a naturally occurring FGF protein. As used herein, reference to a percent (%) identity refers to a BLAST homology search with the default parameters identified in Table 1.

TABLE 1

BLAST Search Parameters

HISTOGRAM

Display a histogram of scores for each search; default is yes.
(See parameter H in the BLAST Manual).
DESCRIPTIONS Restricts the number of short descriptions of matching sequences
reported to the number specified; default limit is 100
descriptions. (See parameter V in the manual page). See also
EXPECT and CUTOFF.
ALIGNMENTS Restricts database sequences to the number specified for
which high scoring segment pairs (HSPs) are reported;
the default limit is 50. If more database sequences than
this happen to satisfy the statistical significance threshold
for reporting (see EXPECT and CUTOFF below), only the
matches ascribed the greatest statistical significance are
reported. (See parameter B in the BLAST Manual).
EXPECT The statistical significance threshold for reporting matches
against database sequences; the default value is 10, such
that 10 matches are expected to be found merely by chance,
according to the stochastic model of Karlin end Altschul (1990).
If the statistical significance ascribed to a match is greater
than the EXPECT threshold, the match will not be reported.
Lower EXPECT thresholds are more stringent, leading to fewer
chance matches being reported. Fractional values are acceptable.
(See parameter E in the BLAST Manual).
CUTOFF Cutoff score for reporting high-scoring segment pairs. The default
value is calculated from the EXPECT value (see above). HSPs are
reported for a database sequence only if the statistical
significance ascribed to them is at least as high as would be
ascribed to a lone HSP having a score equal to the CUTOFF value.
Higher CUTOFF values are more stringent, leading to fewer
chance matches being reported. (See parameter S in the
BLAST Manual). Typically, significance thresholds can be more
intuitively managed using EXPECT.

TABLE 1-continued

BLAST Search Parameters

MATRIX

Specify an alternate scoring matrix for BLASTP, BLASTX,
TBLASTN and TBLASTX. The default matrix is BLOSUM62
(Henikoff & Henikoff, 1992). The valid alternative choices
include: PAM40, PAM120, PAM250 and IDENTITY. No alternate
scoring matrices are available for BLASTN; specifying the
MATRIX directive in BLASTN requests returns an error
response.
STRAND Restrict a TBLASTN search to just the top or bottom strand
of the database sequences; or restrict BLASTN, BLASTX or
TBLASTX search to just reading frames on the top or bottom
strand of the query sequence.
FILTER Mask oil segments of the query sequence that have low
compositional complexity, as determined by the SEG
program of Wootton & Federhen (Computers and Chemistry,
1993), or segments consisting of short-periodicity internal
repeats, as determined by the SNU program of Claverie & States
(Computers and Chemistry, 1993), or, for BLASTN, by the
DUST program of Tetusov and Lipman (in preparation). Filtering
can eliminate statistically significant but biologically
uninteresting reports from the blast output (e.g.. hits against
common acidic-, basic- or proline-rich regions), leaving the more
biologically interesting regions of the query sequence available
for specific matching against database sequences.
Low complexity sequence found by a filter program is substituted
using the letter "N" in nucleotide sequence (e.g.,
"NNNNNNNNNNNNN") and the letter "X" in protein
sequences (e.g., "XXXXXXXXX"). Users may turn off filtering
by using the "Filter" option on the "Advanced options
for the BLAST server" page.
Filtering is only applied to the query sequence (or its translation
products), not to database sequences. Default filtering is DUST
for BLASTN, SEG for other programs.
It is not unusual for nothing at all to be masked by SEG, SNU,
or both, when applied to sequences in SWISS-PROT, so filtering
should not be expected to always yield an effect.
Furthermore, in some cases, sequences are masked in their
entirety, indicating that the statistical significance of
any matches reported against the unfiltered query sequence
should be suspect.
NCBl-gi Causes NCBl gi identifiers to be shown in the output,
in addition to the accession and/or locus name.

Protein homologues of the present invention can be produced using techniques known in the art including, but not limited to, direct modifications to the protein or modifications to the gene encoding the protein using, for example, classic or recombinant DNA techniques to effect random or targeted mutagenesis.

In one embodiment of the present invention, FGF proteins suitable for use in the chimeric FGF protein of the present invention include biologically active FGF proteins that are encoded by a nucleic acid molecule that hybridizes under stringent hybridization conditions to the complementary strand of a nucleic acid molecule encoding FGF-1 or FGF-2. Preferred biologically active FGF proteins for use in a chimeric FGF protein of the present invention include FGF proteins comprising all or a biologically active fragment of an FGF protein including FGF-1 or FGF-2, with FGF-2 being particularly preferred. Other preferred biologically active proteins for use in a chimeric FGF protein of the present invention include FGF proteins comprising all or a biologically active fragment of a protein having an amino acid sequence selected from the group of SEQ ID NO:5, SEQ ID NO:6, SEQ ID NO:7, SEQ ID NO:8, which are amino acid sequences for bovine FGF-2, human FGF-2, bovine FGF-1 and human FGF-1, respectively. In yet another embodiment, an FGF protein suitable for use in a chimeric FGF of the present invention includes an FGF protein having an amino acid sequence corresponding to positions 18 through 172 of SEQ ID NO:2, or to positions 17 through 171 of SEQ ID NO:4. As discussed above, suitable FGF proteins include biologically active fragments and homologues of any of the above identified FGF amino acid sequences and of any other FGF amino acid sequences. Additionally, the nucleic acid and amino acid sequences of many FGF proteins are known in the art, such information being publicly available, for example, on a database such as GenBank. At the time of filing, at least 20 types of FGF have been identified. All known naturally occurring FGF proteins share similar requirements for FGF receptor binding and heparan sulfate dependence, and the use of any of such proteins in a chimeric FGF protein of the present invention results in chimeric FGF proteins having similar advantageous and unexpected properties as those described for the specific penetratin-FGF chimeras disclosed herein. It is noted that in the production of a chimeric FGF protein of the present invention, modifications to the sequences can be made to facilitate the production of the chimera For example, the amino acid sequence of an FGF protein portion of the chimera may be modified to substitute a non-methionine residue for the initial methionine residue to avoid problems with multiple translation start sites in the nucleic acid molecule encoding the chimera. Such modifications are well within the ability of one of skill in the art.

Another portion of a chimeric FGF of the present invention is a penetratin peptide, wherein the penetratin peptide transports the chimeric FGF across a lipid bilayer of a cell independently of the presence of an FGF receptor. According to the present invention, a "penetratin peptide" is an amino acid sequence which is capable of transporting itself and a heterologous protein linked to it across a lipid bilayer or any cellular membrane independent of receptor-mediated or other common endocytic pathways. Therefore, a penetratin peptide does not require a receptor for entry into a cell, nor does it have temperature and energy requirements associated with receptor-mediated or other endocytic biological processes (e.g., the transport can occur at 4° C.). Such penetratin peptides are known in the art, but particularly preferred penetratin peptides for use in the present invention include peptides derived from the helix 3 of the homeobox domain and peptides derived from HIV Tat protein. Helix 3 homeobox peptides and homologues thereof suitable for use in a chimeric protein of the present invention are described in detail in U.S. Pat. No. 5,888,762, 1999 to Joliot et al., PCT Publication No. WO 91/18981 to Centre National de la Recherche Scientifique, PCT Publication No. WO 97/12912 to Centre National de la Recherche Scientifique, each of which is incorporated herein by reference in its entirety. HIV Tat peptides and homologues thereof suitable for use in a chimeric protein of the present invention are described in detail in U.S. Pat. No. 5,804,604, 1998, to Frankel et al., which is incorporated herein by reference in its entirety. Although these publications appreciated the use of penetratin peptides to enable the delivery of a heterologous peptide across a cell membrane independent of a receptor, none of the references disclose the production or use of a chimeric FGF protein of the present invention, and none of the references disclose the unexpected and surprising properties of the chimeric FGF protein of the present invention.

In one embodiment of the present invention, a penetratin portion of a chimeric FGF includes a peptide having an amino acid sequence selected from the group consisting of:

(i) $X_1$-$X_2$-$X_3$-$X_4$-$X_5$-$X_6$-$X_7$-$X_8$-$X9$-$X_{10}$-$X_{11}$-$X_{12}$-$X_{13}$-$X_{14}$-$X_{15}$-$X_{16}$; and, (ii) $X_{16}$-$X_{15}$-$X_{14}$-$X_{13}$-$X_{12}$-$X_{11}$-$X_{10}$-$X_9$-$X_8$-$X_7$-$X_6$-$X_5$-$X_4$-$X_3$-$X_2$-$X_1$;

wherein $X_1$, $X_2$, $X_3$, $X_4$, $X_5$, $X_7$, $X_8$, $X_9$, $X_{10}$, $X_{11}$, $X_{12}$, $X_{13}$, $X_{14}$, $X_{15}$, and $X_{16}$ each represent an α-amino acid, between 6 and 10 of which are hydrophobic amino acids; and wherein $X_6$ represents Trp.

Such a peptide represents a homologue of a helix 3 portion of a homeobox domain protein and is disclosed, for example, in PCT Publication No. WO 97/12912, ibid. In a preferred embodiment, the first peptide is selected from the group of a peptide comprising helix 3 of a homeobox domain and a homeobox domain. As discussed in U.S. Pat. No. 5,888,762, ibid., the term "homeobox peptide" denotes a family of related peptide sequences which occur in various animal species in the products of genes involved in embryogenesis. Genes encoding homeoproteins are expressed at various stages of embryo development and their products control the cell migration and differentiation phenomena involved in the morphogenesis of the organism. Homeobox sequences homologous to that of Drosophila have been found in all vertebrates including mammals. The homeobox sequence encodes a polypeptide sequence of 60 amino acids which corresponds to a structurally and functionally conserved region which is present in all homeoproteins, the homeodomain. The sequence of the homeodomain which is encoded by the homeobox sequence of the Antennapedia gene of Drosophila is represented herein by SEQ ID NO:9. All known homeodomains share the same helix/β-turn/helix structure, despite some differences in their primary sequences. As used herein "helix 3" is defined as the portion of a homeobox peptide (domain), which is involved in the low-affinity binding with the wide groove of DNA. Helix 3 extends from amino-acid 43 to amino-acid 58 of the homeobox peptide (SEQ ID NO:9). Within the context of the present invention "helix 3" also refers to peptides which may slightly differ in their sequence from the helix 3 of naturally occurring homeodomains, provided that the differences do not affect the ability of the peptide to serve as a penetratin peptide in the chimeric protein of the present invention.

Particularly preferred penetratin peptides derived from the helix 3 sequence of a homeobox domain include, but are not limited to: SEQ ID NO:9, amino acid residues 42 through 58 of SEQ ID NO:9, amino acid residues 43 through 59 of SEQ ID NO:9, amino acid residues 43 through 58 of SEQ ID NO:9, amino acid residues 58 through 43 of SEQ ID NO:9, SEQ ID NO:10, SEQ ID NO:11, SEQ ID NO:12, SEQ ID NO:13, SEQ ID NO:14, SEQ ID NO:15, and SEQ ID NO:16. SEQ ID NOs:10–16 are mutants of helix 3 peptides which have penetratin activity and are described in detail in PCT Publication No. WO 97/12912, ibid., and in U.S. Pat. No. 5,888,672, ibid. In a preferred embodiment of the present invention, the first penetratin peptide comprises amino acid residues 2–17 of SEQ ID NO:2.

In another embodiment of the present invention, a penetratin portion of a chimeric FGF can include a peptide comprising amino acid residues 49–57 of HIV Tat protein (SEQ ID NO:17). In a preferred embodiment, such a peptide does not comprise amino acid residues 22–36 or 73–86 of HIV Tat protein (SEQ ID NO:17). Penetratin peptides derived from HIV Tat protein are described in detail in U.S. Pat. No. 5,804,604, ibid., and all of such peptides are incorporated for use in the present invention by reference.

As described in U.S. Pat. No. 5,804,604, Tat protein trans-activates certain HIV genes and is essential for viral replication. The full-length Tat protein is characterized by a basic region which contains two lysines and six arginines (amino acids 49–57) and a cysteine-rich region which contains seven cysteine residues (amino acids 22–37). The basic region (i.e., amino acids 49–57 of SEQ ID NO:17) is thought to be important for nuclear localization (Ruben, S. et al., *J. Virol.* 63: 1–8 (1989); Hauber, J. et al., *J. Virol.* 63 1181–1187 (1989)). Residues 38–58 of SEQ ID NO:17 or protamine, enhance uptake of Tat. Therefore, as shown in U.S. Pat. No. 5,804,604, ibid., the entire 86 amino acids which make up the Tat protein are not required for the uptake activity of Tat. For example, a protein fragment or a peptide which has fewer than the 86 amino acids, but which exhibits uptake into cells and uptake into the cell nucleus, can be used (a functionally effective fragment or portion of Tat).

Preferred peptides derived from HIV Tat protein which are suitable for use in the penetratin portion of a chimeric FGF of the present invention include peptides comprising an amino acid sequence including, but not limited to amino acid residues 37–72 of SEQ ID NO:17, amino acid residues 38–72 of SEQ ID NO:17, amino acid residues 47–72 of SEQ ID NO:17, amino acid residues 37–58 of SEQ ID NO:17, amino acid residues 38–58 of SEQ ID NO:17, amino acid residues 47–58 of SEQ ID NO:17, amino acid residues 1–21 and 38–72 of SEQ ID NO:17, amino acid residues 47–62 of SEQ ID NO:17, amino acid residues 38–62 of SEQ ID NO:17, amino acid residues 1–72 of SEQ ID NO:17, amino acid residues 1–58 of SEQ ID NO:17, and/or amino acid residues 48–60 of SEQ ID NO:17. In a preferred embodiment, such a peptide comprises an amino acid sequence including amino acid residues 48–60 of SEQ ID NO:17 or amino acid residues 2–14 of SEQ ID NO:4.

To produce a chimeric FGF of the present invention, an amino acid sequence comprising a biologically active FGF protein as described above is linked to an amino acid sequence comprising a penetratin peptide as described above. The amino acid sequence of the penetratin portion of the chimera can be linked to either the N-terminal end or the C-terminal end of the FGF protein portion, and preferably, is linked to the N-terminal end of the FGF protein portion. The entire amino acid sequence of the chimeric FGF protein can contain additional amino acid residues other than those included in the FGF protein portion or the penetratin portion. For example, a methionine residue is typically added to the N-terminal end of the entire amino acid sequence encoding the chimeric protein as a translation start codon, such a methionine residue represented in position 1 of both SEQ ID NO:2 and SEQ ID NO:4. Other "linker" amino acid residues may also be introduced to the amino acid construct of the chimera, such as between the FGF portion and the penetratin portions. Such linker residues are used for example, in the TAT-FGF-2 chimera described herein and are represented by amino acid residues 15 and 16 of SEQ ID NO:4. Additional heterologous amino acid sequences may also be introduced into the chimera for the purposes which include, but are not limited to: conformational arrangement of the peptides, facilitation of purification of the chimeric protein, as a marker to track the location of the protein, or for delivery of another substance into a cell. For example, in both the HLX-FGF-2 chimera and the TAT-FGF-2 chimera described herein, a marker peptide derived from human cMyc protein was linked to the C-terminal region of the FGF protein. This portion of the chimeras is represented by amino acid residues 173 to 182 of SEQ ID NO:2 and 172 to 181 of SEQ ID NO:4.

The linkage of a first amino acid sequence comprising a biologically active FGF protein to a second amino acid sequence comprising a penetratin peptide, and/or to other flanking or intervening amino acid sequences to produce a chimeric FGF of the present log invention to produce a molecule of interest can be accomplished by any means which produces a link between the components of the chimera and which is sufficiently stable to withstand the conditions used and which does not alter the desired properties of the chimera (e.g., receptor independence for cellular entry, heparan sulfate independence, fibroblast growth factor biological activity). Preferably, the link between the components of the chimera is covalent. For example, components of a chimeric FGF of the present invention can be linked recombinantly, by joining a nucleic acid molecule encoding an amino acid sequence comprising the penetratin peptide to a nucleic acid molecule encoding an amino acid sequence comprising the FGF protein, and expressing the resulting recombinant nucleic acid molecule in a cell capable of expressing the construct. Alternatively, the two separate nucleic acid sequence can be expressed in a cell individually or the amino acid sequences can be synthesized chemically and subsequently joined, using known techniques. Alternatively, the chimeric FGF of the present invention can be synthesized chemically as a single amino acid sequence (i.e., one in which all components are present) and, thus, joining is not needed.

Coupling of the components of the chimera, when they are produced separately by recombinant or chemical synthesis technology, can be accomplished via a coupling or conjugating agent. Numerous cross-linking agents are known and available in the art. Such reagents include, for example, J-succinimidyl 3-(2-pyridyldithio) propionate (SPDP) or N, N'-(1,3 -phenylene) bismaleimide; N, N'-ethylene-bis-(iodoacetamide) or other such reagent having 6 to 11 carbon methylene bridges; 1,5-difluoro-2,4-dinitrobenzene; p,p'-difluoro-m,m'-dinitrodiphenylsulfone; dimethyl adipimidate; phenol-1,4-disulfonylchloride; hexamethylenediisocyanate or diisothiocyanate, or azophenyl-p-diisocyanate; glutaraldehyde and disdiazobenzidine. Such reagents and methods of using the same will be known to those of skill in the art.

Preferably, a chimeric FGF of the present invention is made using recombinant technology. In one embodiment, a chimeric FGF of the present invention is produced by expressing a recombinant nucleic acid molecule encoding the chimera or a component of the chimera under conditions effective to produce the protein. A preferred method to produce an encoded protein is by transfecting a host cell with one or more recombinant molecules to form a recombinant cell. Suitable host cells to transfect include any bacterial, fungal (e.g., yeast), insect, plant or animal cell that can be transfected. Host cells can be either untransfected cells or cells that are already transformed with at least one nucleic acid molecule.

In one embodiment, a chimeric FGF protein of the present invention is produced by culturing a cell that expresses the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a chimeric FGF protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant chimeric proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein" refers to collecting the whole fermentation medium containing the protein and need not imply additional steps of separation or purification. Proteins of the present invention can be purified using a variety of standard protein purification techniques, such as, but not limited to, affinity chromatography (e.g., heparin affinity chromatography), ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a research or therapeutic reagent.

According to the present invention, a recombinant molecule includes one or more isolated nucleic acid sequences as described herein operatively linked to one or more transcription control sequences. As used herein, the phrase "recombinant molecule" primarily refers to a nucleic acid molecule or nucleic acid sequence operatively linked to a transcription control sequence, but can be used interchangeably with the phrase "nucleic acid molecule". According to the present invention, the phrase "operatively linked" refers to linking a nucleic acid molecule to a transcription control sequence in a manner such that the molecule is able to be expressed when transfected (i.e., transformed, transduced, transfected, conjugated or conduced) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells useful for expressing a linoleate isomerase of the present invention. A variety of such transcription control sequences are known to those skilled in the art. Preferred transcription control sequences include those which function in bacterial, fungal (e.g., yeast), insect, plant or animal cells.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention also contains secretory signals (i.e., signal segment nucleic acid sequences) to enable an expressed protein to be secreted from the cell that produces the protein. Suitable signal segments include a signal segment that is naturally associated with a protein of the present invention or any heterologous signal segment capable of directing the secretion of a protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with a protein of the present invention, or any heterologous leader sequence capable of directing the delivery and insertion of a protein to the membrane of a cell.

Accordingly, one embodiment of the present invention relates to a recombinant nucleic acid molecule encoding a chimeric FGF of the present invention. Such a recombinant molecule includes: (a) a first isolated nucleic acid sequence encoding a biologically active fibroblast growth factor (FGF) protein; and, (b) a second isolated nucleic acid sequence encoding a penetratin peptide that transports said chimeric fibroblast growth factor (FGF) across a lipid bilayer of a cell independently of the presence of an FGF receptor, wherein the second nucleic acid sequence is linked to said first nucleic acid sequence. The first and second nucleic acid sequences are operatively linked to a transcription control sequence. The chimeric fibroblast growth factor (FGF) is characterized by: (i) fibroblast growth factor biological activity in the absence of heparan sulfate; and, (ii) entry into a living cell in the absence of a receptor that binds to FGF. As discussed above with regard to the chimeric FGF protein, it is noted that the recombinant nucleic acid molecule can contain additional nucleic acid sequence encoding linker or heterologous amino acid sequences for purposes which include, but are not limited to: conformational arrangement of the peptides, facilitation of purification of the chimeric protein, as a marker to track the location of the protein, or for delivery of another substance into a cell. For the purpose of conceptualizing the recombinant nucleic acid molecule, such additional nucleotides can be considered to be a portion of the first and/or second nucleic acid sequence discussed above (e.g., nucleotides flanking the nucleotides encoding the FGF protein and/or the penetratin protein) or as additional nucleic acid sequences that flanks and/or connects the first and second sequences.

In accordance with the present invention, an isolated nucleic acid molecule or sequence that encodes an amino acid sequence comprising a biologically active FGF protein or an amino acid sequence comprising a penetratin peptide of the present invention is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated nucleic acid molecule of the present invention can be isolated from its natural source or produced using recombinant DNA technology (e.g., polymerase chain reaction (PCR) amplification, cloning) or chemical synthesis. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Isolated nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode a desired protein of the present invention or to form stable hybrids under stringent conditions with natural gene isolates (i.e., a nucleic acid homologue). An isolated nucleic acid molecule can include degeneracies. As used herein, nucleotide degeneracies refers to the phenomenon that one amino acid can be encoded by different nucleotide codons. Thus, the nucleic acid sequence of a nucleic acid molecule that encodes an FGF protein or a penetratin peptide of the present invention can vary due to degeneracies.

A nucleic acid molecule homologue can be produced using a number of methods known to those skilled in the art (see, for example, Sambrook et al.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Nucleic acid molecule homologues can be selected by hybridization with a gene encoding a naturally occurring gene or by screening the function of a protein encoded by a nucleic acid molecule (e.g., fibroblast growth factor activity).

A first nucleic acid sequence encoding a biologically active FGF protein of a chimeric FGF of the present invention includes a nucleic acid molecule that hybridizes under stringent hybridization conditions to a nucleic acid molecule encoding any naturally occurring FGF protein or fragment thereof, with nucleic acid molecules encoding FGF proteins selected from the group of a fibroblast growth factor-1 (FGF-1) protein and a fibroblast growth factor-2 (FGF-2) protein being particularly preferred. It is noted that such FGF proteins have FGF biological activity. In a preferred embodiment, the first nucleic acid sequence encodes an FGF protein selected from a fibroblast growth factor-1 (FGF-1) protein and a fibroblast growth factor-2 (FGF-2) protein, or a fragment or homologue thereof. In yet another embodiment, the first nucleic acid sequence encodes an FGF protein comprising an amino acid sequence selected from the group consisting of SEQ ID NO:5, SEQ ID NO:6, SEQ ID NO:7 and SEQ ID NO:8. Such sequences have been identified above. Preferably, the first nucleic acid sequence encodes a fibroblast growth factor-2 (FGF-2) protein, or a fragment or homologue of FGF-2. A particularly preferred first nucleic acid molecule comprises from nucleotide 59 to 523 of SEQ ID NO:1 (HLX-FGF-2) or from nucleotide 59 to 523 of SEQ ID NO:3.

A second nucleic acid sequence encoding a penetratin peptide portion of chimeric FGF of the present invention includes a nucleic acid sequence encoding a penetratin peptide having an amino acid sequence selected from the group consisting of:

(i) $X_1$-$X_2$-$X_3$-$X_4$-$X_5$-$X_6$-$X_7$-$X_8$-$X9$-$X_{10}$-$X_{11}$-$X_{12}$-$X_{13}$-$X_{14}$-$X_{15}$-$X_{16}$; and, (ii) $X_{16}$-$X_{15}$-$X_{14}$-$X_{13}$-$X_{12}$-$X_{11}$-$X_{10}$-$X_9$-$X_8$-$X_7$-$X_6$-$X_5$-$X_4$-$X_3$-$X_2$-$X_1$;

wherein $X_1$, $X_2$, $X_3$, $X_4$, $X_5$, $X_7$, $X_8$, $X_9$, $X_{10}$, $X_{11}$, $X_{12}$, $X_{13}$, $X_{14}$, $X_{15}$, and $X_{16}$ each represent an α-amino acid, between 6 and 10 of which are hydrophobic amino acids; and wherein $X_6$ represents Trp.

Particularly preferred penetratin peptides include peptides comprising helix 3 of a homeobox domain and a homeobox domain. Other preferred peptides derived from the helix 3 sequence of a homeobox domain include, but are not limited to: SEQ ID NO:9, amino acid residues 42 through 58 of SEQ ID NO:9, amino acid residues 43 through 59 of SEQ ID NO:9, amino acid residues 43 through 58 of SEQ ID NO:9, amino acid residues 58 through 43 of SEQ ID NO:9, SEQ ID NO:10, SEQ ID NO:1 I, SEQ ID NO:12, SEQ ID NO:13, SEQ ID NO:14, SEQ ID NO:15, and SEQ ID NO:16. Such peptides have described in detail above. In a preferred embodiment, such a nucleic acid sequence encodes a peptide comprising amino acid residues 2–17 of SEQ ID NO:2.

In another embodiment, a nucleic acid sequence encoding a penetratin peptide portion of chimeric FGF of the present invention includes a nucleic acid sequence encoding a penetratin peptide comprising amino acid residues 49–57 of HIV Tat protein (SEQ ID 25 NO:17). In a preferred embodiment, such a peptide does not comprise amino acid residues 22–36 or73–86 of HIV Tat protein (SEQ ID NO:17). Other preferred nucleic acid sequences encode HIV Tat derived peptides including, but not limited to amino acid residues 37–72 of SEQ ID NO:17, amino acid residues 38–72 of SEQ ID NO:17, amino acid residues 47–72 of SEQ ID NO:17, amino acid residues 37–58 of SEQ ID NO:17, amino acid residues 38–58 of SEQ ID NO:17, amino acid residues 47–58 of SEQ ID NO:17, amino acid residues 1–21 and 38–72 of SEQ ID NO:17, amino acid residues 47–62 of SEQ ID NO:17, amino acid residues 38–62 of SEQ ID NO:17, amino acid residues 1–72 of SEQ ID NO:17, amino acid residues 1–58 of SEQ ID NO:17, and/or amino acid residues 48–60 of SEQ ID NO:17. In a preferred embodiment, such a nucleic acid molecule encodes a peptide comprising an amino acid sequence including amino acid residues 48–60 of SEQ ID NO:17 or amino acid residues 2–14 of SEQ ID NO:4.

Particularly preferred nucleic acid sequences encoding penetratin peptides useful in the chimeric FGF of the present invention include nucleotides 11 to 58 of SEQ ID NO:1 (HLX-FGF-2) or nucleotides 14 to 52 of SEQ ID NO:3 (TAT-FGF-2).

Preferred chimeric FGF proteins of the present invention are represented herein as SEQ ID NO:2 and SEQ ID NO:4. The production and characterization of both proteins are described in the Examples section. Specifically, the chimeric protein represented by SEQ ID NO:2 is encoded by a recombinant nucleic acid molecule having a nucleic acid sequence represented by SEQ ID NO:1, and comprises a biologically active FGF-2 protein and a sequence derived from helix 3 of the homeobox domain in Drosophila. The chimeric protein represented by SEQ ID NO:4 is encoded by a recombinant nucleic acid molecule having a nucleic acid sequence represented by SEQ ID NO:3, and comprises a biologically active FGF-2 protein linked via a linker sequence to a peptide derived from HIV Tat.

One embodiment of the present invention relates to a recombinant cell that expresses a recombinant nucleic acid molecule encoding a chimeric FGF of the present invention as described herein. Another embodiment of the present invention relates to a recombinant virus encoding a chimeric FGF of the present invention. A recombinant virus includes a recombinant molecule of the present invention that is packaged in a viral coat and that can be expressed in a cell after delivery of the virus to the cell. A number of recombinant virus particles can be used, including, but not limited to, those based on alphaviruses, baculoviruses, poxviruses, adenoviruses, herpesviruses, and retroviruses. Methods of producing recombinant viruses are well known in the art.

Yet another embodiment of the present invention relates to a therapeutic composition comprising a chimeric fibroblast growth factor of the present invention and a pharmaceutically acceptable excipient, an adjuvant and/or carrier. Suitable excipients include compounds that can be tolerated by the cells and surrounding tissues to which the therapeutic composition is administered. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include a carrier. Carriers include compounds that increase the half-life of a therapeutic composition in the environment to which it is administered. Suitable carriers include, but are not limited to, polymeric controlled release vehicles, biodegradable implants, liposomes, bacteria, viruses, other cells, oils, esters, and glycols.

As discussed above, the chimeric FGF of the present invention provides proteins and recombinant nucleic acid molecules encoding such proteins which are useful in pathological conditions where normal FGF function does occur, but in which exogenously added biologically active FGF would be beneficial, as well as in pathological conditions where normal FGF function does not occur due to biochemical defects in the normal FGF signaling pathways. Therefore, the chimeric FGF is useful for a variety of purposes, including, but not limited to, promoting the healing of wounds, promoting neovascularization, promoting neurogenesis, promoting osteogenesis, promoting ligament and tendon repair, promoting muscle repair and promoting tissue repair during ischaemia and myocardial infarction. Additionally, the chimeric FGF may be useful for treating conditions related to these processes, for enhancing development of cells, and for treating conditions related to FGF protein or receptor defects.

Yet another embodiment of the present invention relates to a method to increase fibroblast growth factor biological activity in a cell. In particular, such a method is useful for repressing terminal differentiation and promoting proliferation in a cell. Such a method includes the step of administering to a cell a chimeric fibroblast growth factor (FGF) protein of the present invention as previously described herein. Such a method is particularly useful in a cell that has a defect in fibroblast growth factor receptors or FGF activity, and includes a cell which has reduced heparan sulfate proteoglycan production characterized by a reduction in both repression of terminal differentiation and promotion of proliferation in the presence of naturally occurring fibroblast growth factor. Such a method is useful when the cell is a cell of a patient that has a condition selected from the group of stroke, nerve damage, bone damage, muscle damage, and a wound. The chimeric FGF can be administered as a therapeutic composition of the present invention.

Accordingly, yet another embodiment of the present invention includes a method to enhance a biological process selected from the group of mitogenesis, angiogenesis, wound healing, neurogenesis, limb patterning, and limb outgrowth, comprising administering to cells associated with the biological process a chimeric fibroblast growth factor (FGF) of the present invention as previously described herein. The chimeric FGF can be administered as a therapeutic composition of the present invention. The therapeutic composition can include other growth factors such as epidermal growth factor (EGF), the transforming growth factors (TGF-α or TGF-β), insulin-like growth factors (IGF-1 and IGF-2), and/or platelet-derived growth factor (PDGF). Therefore, also included within the compositions and methods of the invention are embodiments wherein the chimeric FGF is administered in combination with or in the same treatment protocol with other factors which enhance the beneficial effects of the chimeric FGF or vice versa.

Acceptable protocols to administer therapeutic compositions of the present invention in an effective manner include individual dose size, number of doses, frequency of dose administration, and mode of administration. Determination of such protocols can be accomplished by those skilled in the art. Modes of administration can include, but are not limited to, subcutaneous, intradermal, intravenous, intraperitoneal, topical, intranasal, oral, totransdernal, intraocular and intramuscular routes. A chimeric FGF of the present invention can be administered to cells by in vitro, in vivo, or ex vivo methods.

The following examples are provided for the purposes of illustration and are not intended to limit the scope of the present invention.

EXAMPLES

Example 1

The following example describes the introduction of FGF-2 into cells using penetratin peptides.

To construct a fibroblast growth factor (FGF) capable of receptor-independent translocation across the lipid bilayer, the present inventors chose to fuse either of two distinct penetratin sequences to the amino terminus of FGF-2. One construct contains the penetratin sequence identified in the third alpha helix of the homeodomain in the Drosophila protein Antenapedia (Bloch-Gallego, et al., (1993) *J. Cell Biol.* 120:485–92; Joliot, et al., (1991) *Proc. Nat'l Acad. Sci. USA*, 88:1864–8; Le Roux, et al., (1993) *Proc. Nat'l Acad. Sci. USA*, 90:9120–4; Derossi, et al., (1994) *J. Biol. Chem.*, 269:10444–10450) (HLX-FGF-2) and the second is derived from the HIV Tat protein (Mann, et al. (1991) *Embo Journal*, 10:1733–9; Vives, et al., (1997) *J. Biol. Chem.*, 272:16010–7; Viv s, etal., (1994) *J. Virol.*, 68:3343–53; Frankel, et al., (1988) *Cell*, 55:1189–93) (TAT-FGF-2). The amino terminus was used to avoid possible interference with residues located near the carboxy terminus that contribute to heparan sulfate binding (Presta, et al., (1992) *Biochem. and Biophys. Res. Comm.*, 185:1098–107; Faham, et al., (1996) *Science*, 271:1116–20).

Briefly, the cell-permeable portion of the penetratin-FGF-2 constructs was introduced by PCR utilizing the indicated 5 primers in conjunction with a 3 primer which introduces a single Myc epitope tag at the C-termini of the resulting proteins (Table 2; see SEQ ID Nos:18–27). Useful restriction sites were also designed into the primers to facilitate subcloning. The PCR template employed codes for the 155 amino acid form of human FGF-2 (kindly provided by Scios, Mountain View, Calif.; represented herein as amino acid positions 18 through 172 of SEQ ID NO:2 and amino acid positions 17 through 174 of SEQ ID NO:4). The amplified fragments encoding the various chimeric FGF proteins were subcloned into the expression vector pT7—7 and sequenced for mutations. Proteins were expressed in *E. coli* strain BL2 I (DE3) and purified from cell extracts by heparin affinity chromatography. Biological activity of the penetratin-FGF-2 proteins was determined by the MM14 thymidine incorporation assay (described below in Example 2).

sought to determine whether one or both of these events could be mediated by FGF translocated to an intracellular location or compartment.

TABLE 2

Nucleotide sequence of primers used to create the
penetratin-FGF-2 constructs and the corresponding amino acid sequence.

3-primer (LOWER SEQUENCE): C-termini of FGF-2 + Myc Tag)

```
                                                           HindIII
5' CCA ATG TCT GCT AAG AGC GAA CAG AAA CTC ATC TCT GAA GAG GAT CTG TGA AAG CTT GGG     SEQ ID NO:18
3' GGT TAC AGA CGA TTC TCG TCG CTT TTT GAG TAG AGA CTT CTC CTA GAC ACT TTC GAA CCC     SEQ ID NO:20
      P   M   S   A   K   S   E   Q   K   L   I   S   E   E   D   L   *                SEQ ID NO:19
         FGF-2                                            Myc Tag
```

TAT-5

```
             NdeI                                                         EcoRI
5' G GTA GTC CAT ATG GGC CGC AAA AAA CGC CGC CAG CGC CGC CGC CCG CCG CAG GAA TTC C     SEQ ID NO:21
                                                         GGC GGC GTC CTT AAG G 5'      SEQ ID NO:23
                  M   G   R   K   K   R   Q   R   R   R   P   P   Q   E   F            SEQ ID NO:22
```

FGF-25 EcoRI(MA)

```
      EcoRI                                                                             SEQ ID NO:24
5' G GAA TTC GCG GCT GCT GGT TCT ATC
      E   F   A   A   A   G   S   I                                                    SEQ ID NO:25
```

HLX(MA)-5

```
              NdeI
5' G GTA GTC CAT ATG AGA CAG ATC AAG ATC TGG TTT CAG AAC CGG CGC ATG AAG TGG AAA AAG
                  M   R   Q   I   K   I   W   F   Q   N   R   R   M   K   W   K   K
                                                  HLX
   GCG GCT GCT GGT TCT ATC AC 3'                                                       SEQ ID NO:26
    A   A   A   G   S   I                                                              SEQ ID NO;27
       FGF-2
```

Example 2

The following example demonstrates that the binding and biological activity of penetratin-FGF-2 fusion proteins are indistinguishable from wild type FGF-2.

For the following experiments, the present inventors utilized a skeletal muscle cell line (MM14) to investigate FGF signaling (Linkhart, et al., (1980) *J. Supramol Struct*, 14:483–98). Of particular interest is the activation of distinct signaling pathways by a single FGF receptor in the se cells (Templeton, et al., (1992) *Dev Biol*, 154:169–81). Addition of exogenous FGF is required to repress terminal differentiation and promote proliferation (Clegg, et al., (1987) *J. Cell Biol.*, 105:949–956; Linkhart, et al., (1980) *J Supramol Struct*, 14:483–98). These pathways can be distinguished by removing serum from the growth medium, where in the presence of FGF, terminal differentiation is repressed while proliferation ceases (Clegg, et al., (1987) *J. Cell Biol.*, 105:949–956). Additionally, recent chimeric receptor studies from the present inventors' laboratory demonstrated that activation of the FGF receptor tyrosine kinase is sufficient to mediate repression of differentiation but fails to stimulate proliferation (Kudla, et al., (1998) *J. Cell Biol.*, in press). Whether or not the receptor itself plays a role in the FGF derived signal that mediates cellular proliferation remains unclear. Studies using FGF-1 conjugated to diptheria toxin suggest that intracellular FGF is capable of stimulating DNA synthesis (Wiedlocha, et al., (1994) *Cell*, 76:1039–1051). Other studies suggest that intracellular translocation of the receptor and ligand to the nucleus is necessary for the intracellular actions of FGFs (Prudovsky, et al., (1994) *J. Biol. Chem.*, 269:31720–31724). Since MM14 cells display two independent FGF signaling events, the present inventors sought to determine whether one or both of these events could be mediated by FGF translocated to an intracellular location or compartment.

To examine the interaction between the penetratin FGF-2 chimeras and the FGF receptor125I-labeled chimeric or wild type FGF-2 were covalently crosslinked to cell surface FGF receptors (FGFRs) present on intact MM14 cells (a mouse myoblast cell line). The various forms of FGF-2 were iodinated by brief incubation with ChloramineT/$^{125}$I-sodium iodide and purified by heparin affinity chromatography as previously described (Rapraeger, et al., (1994) *Meth. Enzymol.*, 245:219–240). Crosslinking of the various $^{125}$I-labeled FGFs to MM14 cell surface receptors was carried out essentially as previously described (Olwin, et al., (1986) *Biochemistry*, 25:3487–3492).

Briefly, MM14 cells were grown to approximately 500,000 cells per 100 mm plate and incubated with or without 30 mM sodium chlorate 3 hrs prior to initiation of FGF binding. In all of the examples presented herein, all cells were grown in a humidified incubator maintained 37° C. in an atmosphere of 5% $CO^2$. Unless otherwise noted, all cells were grown in the presence of 100U penicillin G and 5 μg streptomycin sulfate per ml of media. MM14 myoblasts were cultured on gelatin coated plates in growth media consisting of Hams F10C supplemented with 15% horse serum (HS) in the presence of 0.3–2.5 nM FGF-2 (purified from a yeast strain expressing human FGF-2 (Rapraeger, et al., (1994) *Meth. Enzymol.*, 245:219–240) with increasing cell density. FGF-2 was added every 12 hours and the growth media replaced at 24 hour intervals.

In this experiment, cells were washed 3 times in ice cold binding buffer (25 mM HEPES (pH7.4), 0.2% BSA in F10C), followed by the addition of radiolabeled FGF in binding buffer (final concentration of 20 pM) in the presence or absence of 50 nM unlabeled FGF-2. After 2.5 hrs at 4° C., unbound ligand was removed from the cells by 3 rapid washes with ice cold wash buffer(150 mM NaCl in 25 mM HEPES (pH7.4)). Cells were then subjected to a 30 min incubation with ice cold 0.3 mM DSS in wash buffer. Following the DSS incubation, cells were washed 3 times with ice cold wash buffer and scraped off of the plates into 1 ml wash buffer supplemented with 1 mM EDTA, 1 mM PMSF, 1 µg/ml leupeptin and 1 µg/ml aprotinin. Following a brief centrifugation, the wash buffer was removed and the cells were lysed with the protease inhibitor supplemented wash buffer containing 1% Triton X-100 and 1X SDS-reducing buffer. Samples were separated by SDS-PAGE and crosslinked materials visualized by autoradiography.

Binding and crosslinking of the penetratin FGF-2 fusions mirrored that of wild type FGF-2 both in the absence and presence of unlabeled FGF-2 competitor (data not shown). The wild type, HLX-FGF-2, and TAT-FGF-2 crosslinked to receptors of approximately 130 kDa. Moreover, the binding of each protein was dependent on the presence of cell surface heparan sulfate, demonstrating that the penatratin fusion proteins and wild type FGF-2 exhibit indistinguishable cell surface binding characteristics.

The biological activity of purified HLX-FGF-2 and TAT-FGF-2 was compared to wild type FGF-2 by examining the ability of each to promote DNA synthesis in MM14 skeletal muscle cells. These cells are absolutely dependent on addition of exogenously applied FGFs to (1) repress terminal differentiation, and (2) to promote proliferation. The protein concentration of HLX-FGF-2 and TAT-FGF-2 was determined and the specific activity compared to parental FGF-2 on MM14 cells as follows.

Cell cycle exit was assessed essentially as described previously [Olwin, 1986#6411. MM14 cells were plated at 2500 cells per well in growth media on gelatin coated 24 well plates. Additions were then made as indicated in the figure legends and the cells were incubated for approximately 16 hours. Two µCi of [methyl-$^3$H] thymidine was then added to each well followed by an additional 6 hour incubation. The media was then removed, followed by cell lysis and DNA precipitation facilitated by the addition of an aqueous solution of 2% TCA and 0.1% sodium pyrophosphate. After 5 min at 4° C., the TCA solution was removed and the precipitate washed twice with 4° C. 70% ethanol. The precipitates were then resuspended in 0.5 M NaOH and combined with scintilation fluid for quantitation of the incorporated $^3$H-thymidine.

In agreement with the binding data, this experiment demonstrated that all three proteins (wild type, HLX-FGF-2, and TAT-FGF-2) were equally active in stimulating cellular proliferation as demonstrated by similar DNA synthesis dose response curves in MM14 cells (data not shown).

Example 3

The following example demonstrates that the cell-permeable peptides of the FGF chimeras facilitate receptor-independent chimeric FGF-2 uptake.

To establish that the penetratin peptide portion of the chimeric FGF-2 constructs was capable of translocating the attached FGF-2 cargo across the lipid bilayer of the plasma membrane, myoblast cells lacking FGF receptors (L6A1 (FR-)) were incubated with $^{125}$I-labeled penetratin chimeras (described in Examples 1 and 2) at 4° C. Following a 4 hr incubation, cell-surface bound $^{125}$I-labeled material was removed by washing in a high stringency buffer, the cells were lysed, and the $^{25}$I-labeled material associated with the cellular interior was counted in a scintillation counter.

At 4° C., approximately 10–20% of the applied penetratin-FGF-2 chimeras' $^{125}$I-cpm were found associated with the cell interior, whereas<2% of the wild type FGF-2's $^{125}$I-cpm were localized to the cell interior (FIG. 1). Therefore, both of the penetratin-FGF-2 chimeras effectively enter the cell at 4° C., in support of an internalization mechanism facilitated by the penetratin sequences and not an endogenous cellular process.

Example 4

The following example demonstrates that removal of cell surface binding sites for FGF fail to abolish the signaling capacity of chimeric FGF-2 molecules.

A number of studies have suggested that FGF-2 provides critical signals via intracellular mechanisms that are FGF receptor independent. To test this hypothesis, it was determined whether HLX-FGF-2 or TAT-FGF-2 were capable of promoting a biological response in cells where the FGF receptors have been removed and the cells no longer respond to exogenously applied wild type FGF-2.

For this experiment, MM14 cells were enzymatically treated to temporarily remove FGF receptors. Because these cells exhibit a rapid and irreversible commitment to terminal differentiation in the absence of FGF, they are an ideal choice to test the hypothesis. Moreover, the present inventors have previously demonstrated that repression of myogenesis and stimulation of proliferation by FGFs are mediated by distinct FGF-dependent intracellular signals. Rapid irreversible differentiation in MM14 cells can be best visualized by utilizing cells synchronized at the M/G1 boundary by mitotic shake-off. If withdrawn from FGF for~3 h (the duration of the G1 phase), the cells will irreversibly commit to terminal differentiation, fail to enter into S-phase and express skeletal muscle genes within 6 h whether or not FGFs are added after the initial withdrawal period. Thus, cells synchronized by mitotic shake-off and plated at clonal density in the absence of FGF for 3 h will permanently exit the cell cycle and differentiate as single cells. Taking advantage of this rapid FGF-dependent response, the present inventors asked if trypsin-treated MM14 cells synchronized at the MlG 1 boundary were capable of responding to FGF-2 or the penetratin-FGF2 fusions.

Figure 2:
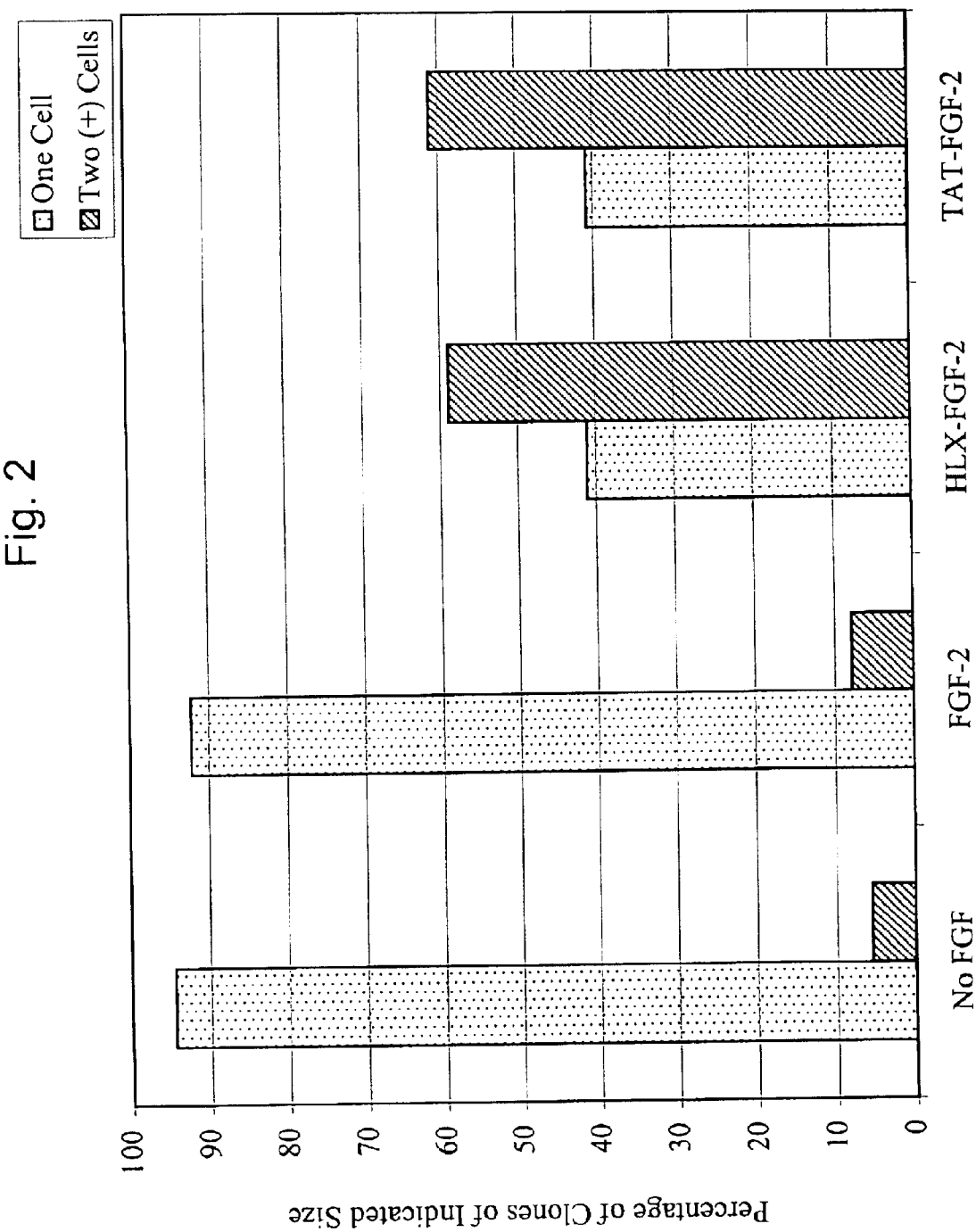
FIG. 2 is a graph showing that synchronized MM14 cells subjected to trypsin treatment to remove extracellular receptors proliferate in response to chimeric, but not wild type, FGF-2.

Synchronized mitotic MM14 cells were trypsin treated, exposed to the various FGFs for 1 h in solution, trypsin treated again and then plated at clonal density in the absence of FGF and in the presence of a blocking FGF-2 antibody. Briefly, mitotic MM14 cells were collected from the media of cells grown to densities of approximately 500,000 cells/100 mm plate after the plates were gently rocked to dislodge cells undergoing mitosis. After a 5 min centrifugation at 1,000×g, the cells were washed with phosphate buffered saline (PBS), recentrifuged and then resuspended in a solution of 0.05% trypsin, 0.53 mM EDTA in PBS and incubated at 37° C. for 10 min. Hams F10C supplemented with 15% HS was then added and the cells centrifuged as before. Cells were then resuspended in fresh F10C supplemented with 15% HS and aliquoted into 1.5 ml microfuge tubes. Additions were then made as indicated in FIG. 2, followed by an incubation for 1 hr at 37° C. Cells were then collected by centrifugation, washed with PBS and treated again with 0.05% trypsin, 0.53 mM EDTA in PBS for 10 min at 37° C. The trypsin was then inactivated by the addition of F10C supplemented with 15% HS and the cells plated at clonal density (50–100 cells per well) on 6 well gelatin coated plates. Cells were grown undisturbed for 36 hour and then fixed with 70% ethanol and stained for scoring with Mayers hematoxylin. Cells were scored for the number of cells/clone.

The first trypsin treatment is expected to remove cell surface FGFR1 and heparan sulfate proteoglycans, both of which are necessary for FGF signaling. The second trypsin plus antibody treatment should eliminate or block remaining extracellular FGFs that were not removed following the wash procedure. Thus, the only FGFs present should be those that have been internalized (i.e., TAT-FGF-2 or HLX-FGF-2). If intracellular TAT-FGF-2 and HLX-FGF-2 are active, it is expected that these FGFs will promote at least one cell cycle. In the absence of additional FGF-2, it is unlikely that the cells would respond for more than one cell cycle.

FIG. 2 shows the results from at least 90 clones per treatment and is representative of several independent experiments. FIG. 2 shows that wild type FGF-2 was unable to to promote proliferation of synchronized, trypsin-treated MM14 cells. However, both the TAT-FGF-2 and HLX-FGF-2 fusion proteins promoted cell division, consistent with a site of intracellular action for these factors (FIG. 2). Similar experiments were performed using [$^3$H]thymidine and DNA synthesis, and results were obtained that were consistent with the clonal assay data (not shown).

Example 5

The following example shows that inhibition of heparan chain sulfation by chlorate treatment is not sufficient to completely block chimeric FGF-2 signaling in MM14 cells.

Activation of cell surface FGF receptor I (FGFR1) by FGFs, leading to repression of differentiation and promotion of DNA synthesis, is absolutely dependent on the presence of heparan sulfate proteoglycans. The previous experiment suggested that HLX-FGF-2 and TAT-FGF-2 can act at an intracellular location that is independent of cell surface FGFR1. As such, the requirement for heparan sulfate as has been demonstrated for wild-type FGF-2 was investigated for the penetratin-FGF-2 chimeras. The heparan sulfate requirement for HLX-FGF-2, TAT-FGF-2 and wild type FGF-2 was examined by treating MM14 cells with sodium chlorate and quantitating the extent of cell proliferation (FIG. 3) and DNA synthesis (FIGS. 4A and 4B) in the absence or presence of added exogenous heparin.

Figure 3:
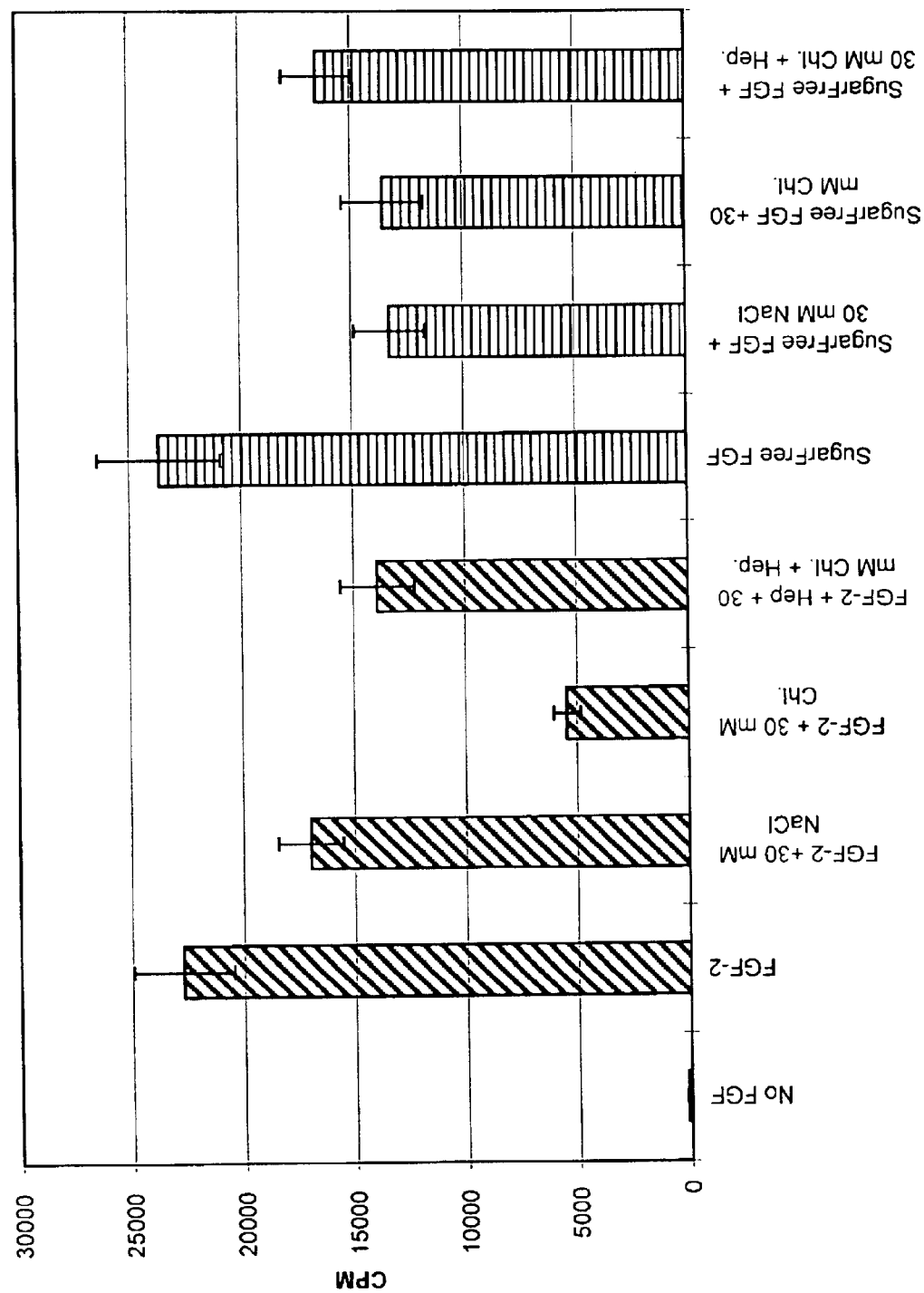
FIG. 3 is a graph showing that a mouse myoblast cell line (MM14) requires the s presence of heparan sulfates (or heparin) in order to respond to FGF and grow (as measured by the incorporation of radioactivity into DNA (CPM)).

FIG. 3 shows that the addition of heparin (Hep.) along with FGF-2 allows the cells to grow essentially normal. However, cells treated with both sodium chlorate and penetratin-FGF-2 chimeras continue to grow normally in the presence or absence of heparin. In this experiment, it was noted that sodium chloride (NaCl), a compound which has no direct effect on FGF-stimulated growth, may be preventing maximal growth due to the high ionic strength.

As shown in FIGS. 4A and 4B, incubation of MM14 cells with sodium chlorate during the time course of a cell cycle exit assay substantially inhibits DNA synthesis in cells treated with either 200 pM or 2 nM wild type FGF-2. Data for both HLX-FGF-2 (FIG. 4A) and TAT-FGF-2 (FIG. 4B) is represented as percent maximal DNA synthesis for the chlorate treated cells. Inclusion of 10 g/ml heparin overcomes this DNA synthesis block and allows the cells to respond in a manner similar to non-treated cultures (FIGS. 4A and 4B). However, chlorate-treated MM14 cells respond to TAT-FGF-2 and HLX-FGF-2 in the absence of heparin, demonstrating that the activity of these factors do not exhibit the strict heparan sulfate dependency seen for wild type FGF-2 (FIGS. 4A and 4B). These factors are, however, to somewhat sensitive to the presence of heparan sulfate since DNA synthesis in the presence of chlorate is approximately 50–60% of that observed in the absence of chlorate or the presence of heparin (FIGS. 4A and 4B). Note that the binding of the FGF-2 fusion proteins to cell surface FGFR1 was heparan sulfate dependent (Example 2), demonstrating that the cell surface binding and biological activity of TAT-FGF-2 and HLX-FGF-2 do not necessarily correlate. Thus, these data indicate that HLX-FGF-2 and TAT-FGF-2 act at an alternate site and agree with the present inventors' data suggesting an intracellular site of action.

Example 6

The following experiment shows that the cell-permeable peptide portion of the chimeric FGFs fails to alter the oligomerization state of the proteins relative to wild type FGF-2.

It is possible that the binding of the penetratin fusions to FGFR1 differs from wild type FGF-2. Although the oligomeric state of FGF bound to its receptor remains unclear, published data suggests that multimerization, perhaps facilitated by the heparan sulfate chains, is required for receptor mediated signaling (Moy, et al., (1997) [published erratum appears in Biochemistry 1997 Jun 24;36(25):7936] *Biochemistry*, 36:4782–91; Herr, et al., (1997) *J Biol Chem*, 272:16382–9; Venkataraman, et al., (1999) *Proc. Nat'l Acad. Sci. USA*, 96:1892–7). It is possible that the penetratin-FGF-2 fusion proteins could overcome a requirement for heparan sulfate by dimerizing or forming multimeric complexes. As such, increasing concentrations of $^{125}$I-radiolabeled FGF-2, HLX-FGF-2 and TAT-FGF-2 were incubated with the chemical crosslinking reagent DSS to determine if the addition of the penetratin peptides promoted the formation of multimeric complexes. Briefly, approximately 2 femtomole of $^{125}$I-labeled wild type or penetratin FGF-2 was mixed with varying amounts of unlabeled wild type FGF-2 in crosslinking buffer (20 mM HEPES (pH 7.4), 300 mM NaCl, 0.3 mM disucciminidyl suberate (DSS)) to yield the desired concentrations. The reaction mixtures were incubated 2 hrs at room temperature followed by the addition of Tris.HCl (pH 8.0) to a final concentration of 150 mM to quench the reactions. The products were then precipitated by the addition of trichloroacetic acid (TCA) to 10%, collected by centrifugation at 16,000×g, resuspended in 1× SDS reducing buffer (2% SDS, 10% glycerol, 0.3% 2-mercaptoethanol, 0.1% bromophenol blue in 50 mM Tris.HCl (pH 6.8)), separated by SDS-PAGE and visualized by autoradiography.

The results indicated that the predominant form of both HLX-FGF-2 and TAT-FGF-2 is monomeric with a small portion of molecules existing as dimers or trimers (data not shown), The relative distribution of multimers appears to be indistinguishable between wild type FGF-2 and the penetratin-FGF-2 chimeras (data not shown). Without being bound by theory, the present inventors believe that this data show that it is unlikely that the activity of the chimeric FGF-2 proteins in the absence of heparan sulfate is due to the ability of the penetratin fusion proteins to form dimeric or oligomeric complexes.

Example 7

The following example demonstrates that the intracellular effects of chimeric FGF-2 appear to require the presence of a functional FGF receptor.

In the examples above, the present inventors have demonstrated that TAT-FGF-2 and HLX-FGF-2 act at a site that is independent of cell surface FGF receptors. However, since the cells used for these experiments possess FGF receptors, it is important to determine if the penetratin-FGF-2 fusions are capable of mediating cellular responses in cells devoid of FGF receptors. As such, two cell lines devoid of endogenous FGFRs were employed. The first cell line, L6A1(FR-), is a skeletal muscle cell line that expresses cell surface heparan sulfate proteoglycans but was selected for lack of FGFR expression (see Example 3). The second cell line is a lymphoid cell line (BaF3), which expresses neither FGFRs nor heparan sulfate proteoglycans.

First, it was determined whether addition of TAT-FGF-2 or HLX-FGF-2 to L6A1 (FR-) cells could promote DNA synthesis. L6A1(FR-) cells were originally selected by their ability to grow in the presence of an FGF-2-saporin toxin conjugate and subsequently grown in DMEM supplemented with 10% fetal bovine serum (FBS) (B. B. Olwin, unpublished data). In this experiment, L6A1(FR-) cells were plated at 50,000 cells per well in DMEM supplemented with 10% FBS in 96 well plates and incubated for 24 hours. Cells were then starved by replacing the growth media with DMEM supplemented with 0.1% FBS. After 48 hours in starvation media, the cells were stimulated for 24 hours with the indicated additions (FIG. 5A) in the presence of starvation media. One $\mu$Ci of [methyl-$^3$H] thymidine was then added to each well and the cells incubated for an additional 6 hours. Cells were then processed as described for the MM14 cell cycle exit assay.

As shown in FIG. 5A, addition of serum to these cells promotes cell proliferation and represses terminal differentiation similar to the cellular responses of MM14 skeletal muscle cells to FGF-2. Unexpectedly, however, the addition of TAT-FGF-2 or HLX-FGF-2 failed to promote DNA synthesis (FIG. 5A), which suggests that FGF receptors may be required for the action of the penetratin chimeras. However, it was possible that the selection procedure for isolating L6 cells devoid of FGF receptors may have altered the cellular response to FGFs.

Therefore, we tested the ability of IL-3-dependent BaF3 cells to respond to penetratin-FGF-2. Cell viability was determined for BaF3 cells or their transfected variants with a Promega Cell Titer assay kit. Briefly, 20,000/well were plated in RPMI medium supplemented with 10% BCS with the indicated additions (FIGS. 5B and 5C) in 96 well plates and grown for 72 hrs. Cell viability was then assessed using a tetrazolium dye-based assay (Promega Cell Titer Assay Kit). Briefly, the Cell Titer MMT dye reagent was added followed by a 4 hr incubation at 37° C. The resulting purple precipitate was then solubilized by the addition of an organic solvent (Cell Titer Solubilization reagent) and the absorbance at 595 run was measured to assess cell viability. WEHI-3 cells (Palacios, et al., (1985) *Cell*, 41:727–34) were grown to high density in Dulbecco s modified Eagle s medium (DMEM) supplemented with 10% bovine calf serum (BCS). The interleukin-3 (IL-3) containing WEHI-3 conditioned media was collected, filtered and utilized for the growth of BaF3 cells (Palacios, et al., (1985) *Cell*, 41:727–34; Mathey-Prevot, et al., (1986) *Mol. Cell. Biol.*, 6:4133–5). BaF3 cells and their transfected derivatives were grown in RPMI medium supplemented with 10% BCS and 15% WEHI-3 conditioned media (WCM) (FIGS. 5B and 5C).

Figure 5C:
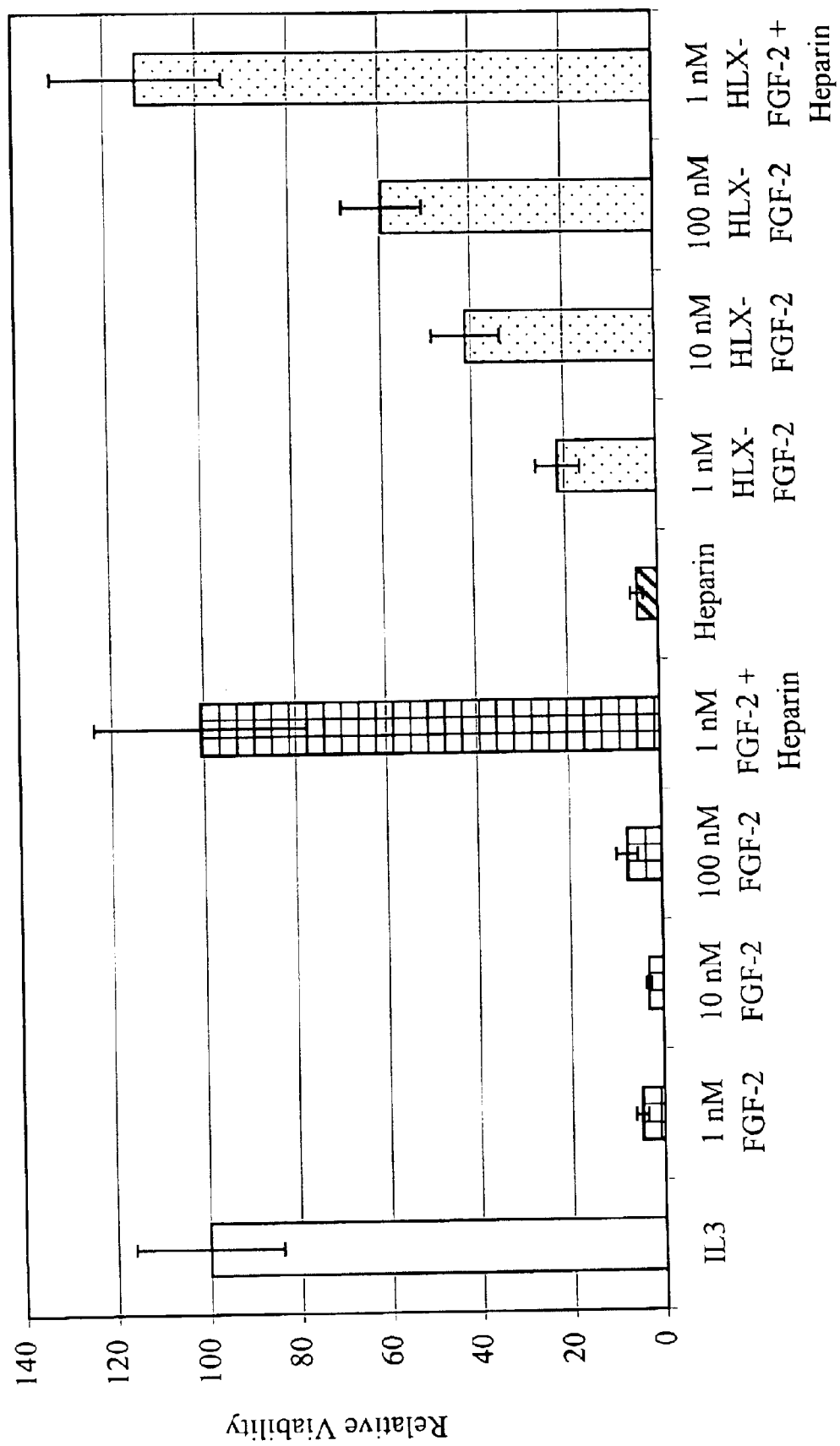
FIG. 5C is a graph showing that chimeric FGF-2 functions in BaF3 cells stably of transfected with an expression construct encoding FGF receptors.

FIG. 5B shows that parental BaF3 cells were unresponsive to either FGF-2 or HLX-FGF-2 in the presence or absence of added heparin, conclusively demonstrating that the penetratin FGF-2 fusions are not active in cells lacking FGF receptors. If transfected with FGFR1, BaF3 cells can be relieved of their requirement for IL-3 in the presence of both FGF-2 and heparin. Thus, tonsure that penetratin-FGF-2 is active in the presence of FGFR1 in the context of the BaF3 cell line, BaF3 cells stably transfected with an FGFR1 expression construct (Ornitz, et al., (1996) *J Biol Chem*, 271:15292–7) were tested for their ability to respond to either FGF-2 or HLX-FGF-2 in the presence and absence of heparin. FIG. 5C demonstrates that FGF-2 and HLX-FGF-2 were both able to relieve the IL-3 dependence of BaF3 cells expressing FGFR1 in the presence of heparin. In the absence of heparin, wild type FGF-2 fails to maintain cell viability (FIG. 5C), consistent with previous reports. However, HLX-FGF-2 is capable of relieving the IL-3 dependency in BaF3 cells expressing FGFR1 even in the absence of heparin (FIG. 5C). Although the HLX-FGF-2 penetratin fusion exhibits an enhanced response in the presence of heparin, it does not require heparin for maintaining BaF3 cell viability in FGFR1 transfectants. These data agree with the MM14 data (Example 5) where HLX-FGF-2 and TAT-FGF-2 did not exhibit an absolute dependence on the presence of heparan sulfate. Together, these data strongly indicate that the penetratin fusions are absolutely dependent on FGFRs for mediating their biological activity. However, these proteins do not require the presence of FGF receptors on the cell surface to promote DNA synthesis and repress myogenic differentiation. Following ligand-induced internalization, active FGFR1 translocates to a perinuclear location in 3T3 cells, where the active ligand-receptor complex is proposed to play a role in cellular proliferation (Prudovsky, et al., (1994) *J. Biol. Chem.*, 269:31720–31724). These studies are consistent with these results and suggest that intracellular FGF-2 requires an intracellular FGFR1 to function.

Example 8

The following example shows that an FGF receptor that lacks tyrosine kinase shows repressed differentiation in the presence of a penetratin-FGF-2.

Figure 6:
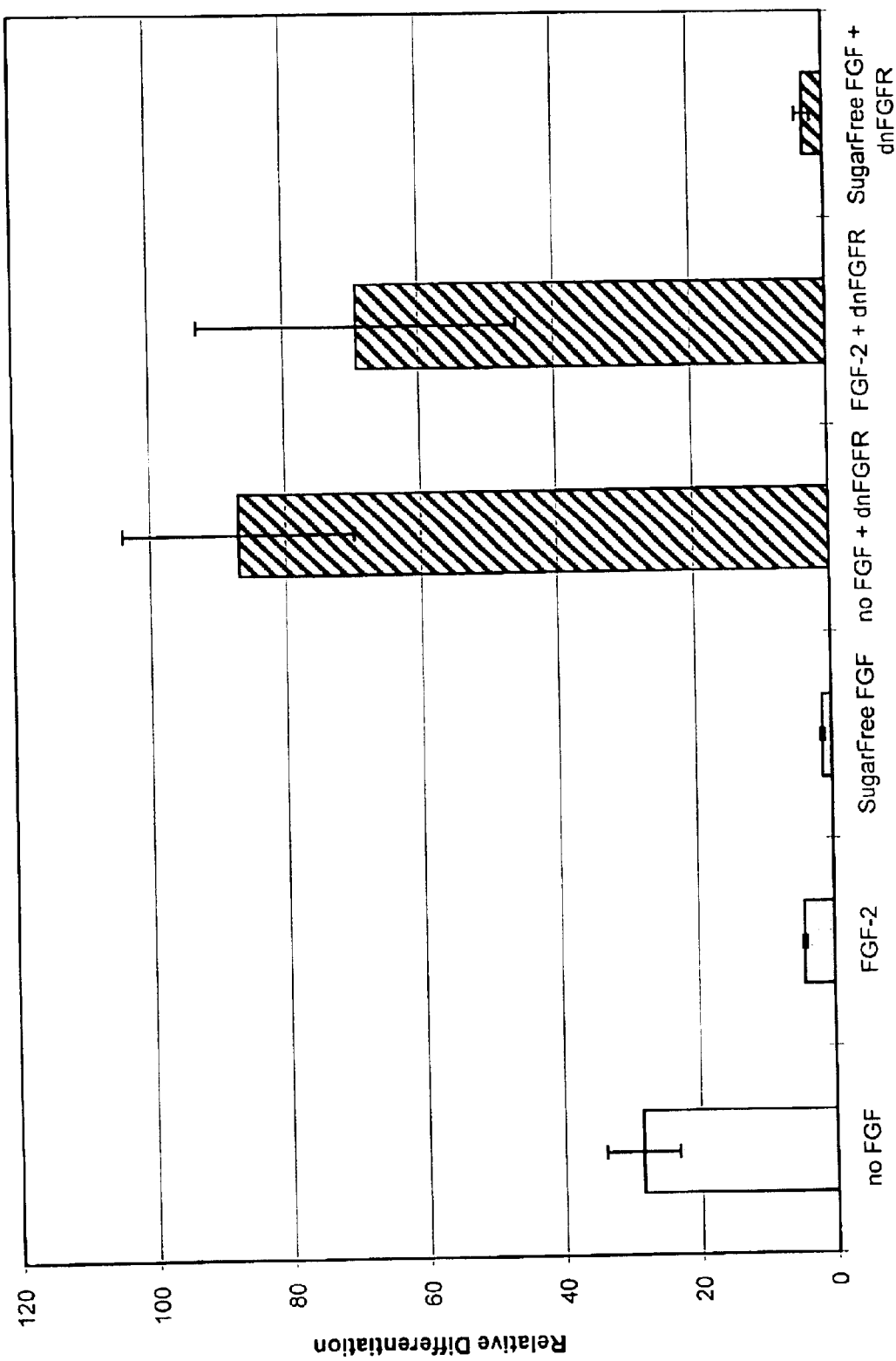
FIG. 6 is a graph illustrating that MM14 cells expressing an FGF receptor lacking tyrosine kinase (dnFGFR) show repressed differentiation in the presence of HLX-FGF-2, but not in the presence of wild type FGF-2.

In these experiments, the present inventors investigated whether the kinase portion of the FGF receptor was required for the penetratin-FGF chimeras to function. A gene that encodes an FGF receptor lacking the tyrosine kinase (referred to as the dominant negative FGF receptor or dnFGFR) was introduced into and expressed in MM14 cells. In MM14 cells, expression of dnFGFR blocks the ability of the wild type FGF-2 to stimulate proliferation and inhibit differentiation. FIG. 6 shows, however, that the HLX-FGF-2 chimera, however, was able to overcome the effect of the kinase deleted FGF receptor.

Figure 7A:
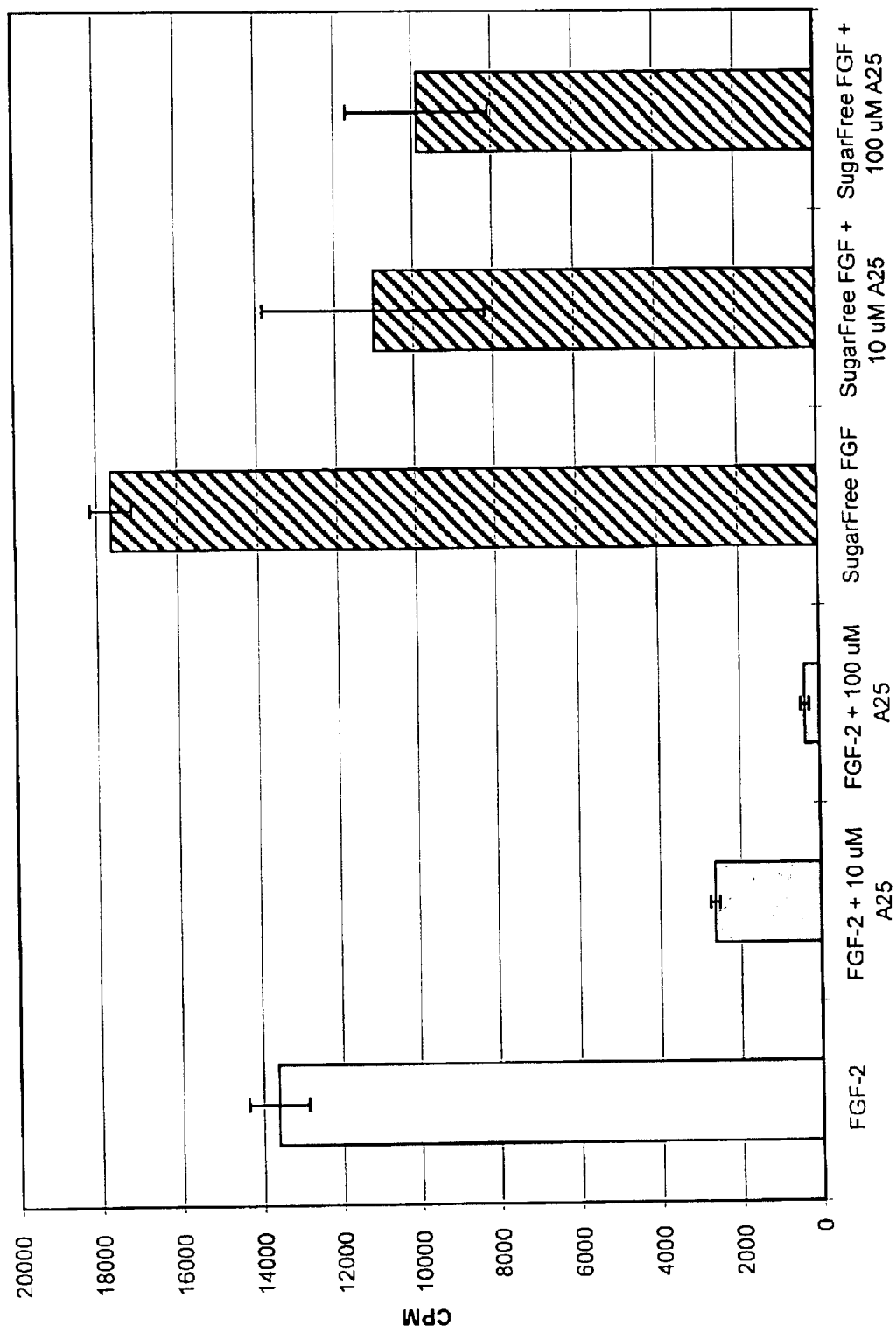
FIG. 7A is a graph showing that in MM14 cells treated with Tyrphostin A25, growth is substantially inhibited in cells treated with FGF-2, but not in cells treated with HLX-FGF-2.

Another series of experiments was carried out to further demonstrate the unique properties of the HLX-FGF-2 chimera by examining the requirement of tyrosine phosphorylation for FGF biological action. The FGF receptor is a tyrosine kinase (capable of phosphorylating tyrosine residues on certain proteins). Numerous chemical compounds are available to block tyrosine kinases and hence inhibit their biological action. A series of inhibitors referred to as Tyrphostins have been widely used to block tyrosine kinase activities. FIGS. 7A and 7B show that two Tyrphostin derivatives, A25 and B42, were both effective at inhibiting proliferation in wild type FGF-2 treated MM14 cells. However, neither of these inhibitors were effective at blocking proliferation in MM14 cells treated with HLX-FGF-2 (FIGS. 7A and 7B).

Example 9

The following example shows that receptor phosphorylation is required for chimeric FGF function.

The requirement of intracellular but not extracellular FGF receptor for HLX-FGF-2 and TAT-FGF-2 function may reflect a requirement for subcellular localization of the penetratin fusions or a requirement for FGF receptor signaling by the fusion proteins or a combination of both. To distinguish between these possibilities, the activity of the penetratin fusions was tested in the presence of two distinct tyrosine kinase inhibitors, Tyrphostin AG1296 (Kovalenko, et al., (1994) *Cancer Res.*, 54:6106–14) and Sugen SU4984 (Mohammadi, et al., (1997) *Science*, 276:955–60). While Tyrphostin AG1296 is reported to be a selective, potent inhibitor of PDGF-mediated signaling, it has also been reported to inhibit FGF-mediated signaling. MM14 cells lack PDGF receptors and fail to respond to PDGF treatment and as such, Tyrphostin AG1296 was expected to be useful for examining the role of the FGF receptor in penetratin-FGF signaling. Sugen SU4984 is a potent inhibitor of the FGF receptor kinase activity and therefore was a useful tool to investigate the requirement for FGFR phosphorylation in penetratin-FGF action. Furthermore, SU4984 has been shown to effectively block the in vivo action of FGFR1 and FGFR2 in Xenopus laevis limb regeneration (D'Jamoos, et al., (1998) *Wound Repair Regen*, 6:388–97).

Figure 8A:
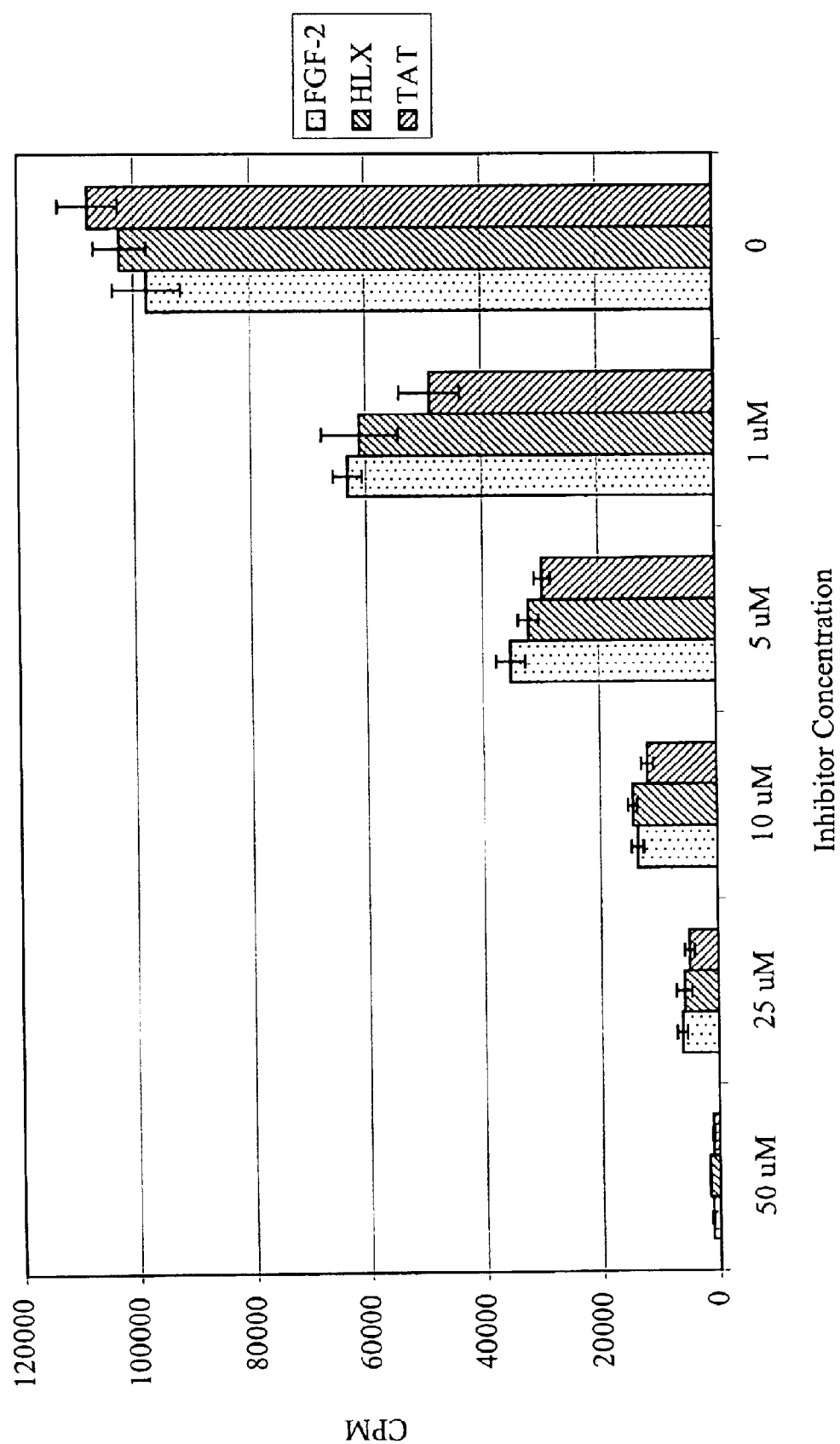
FIG. 8A is a graph demonstrating that treatment of cells with tyrosine kinase inhibitor Tyrphostin AG1296 in the presence of wild type FGF-2, TAT-FGF-2, or HLX-FGF-2, effectively blocked DNA synthesis.
Figure 8B:
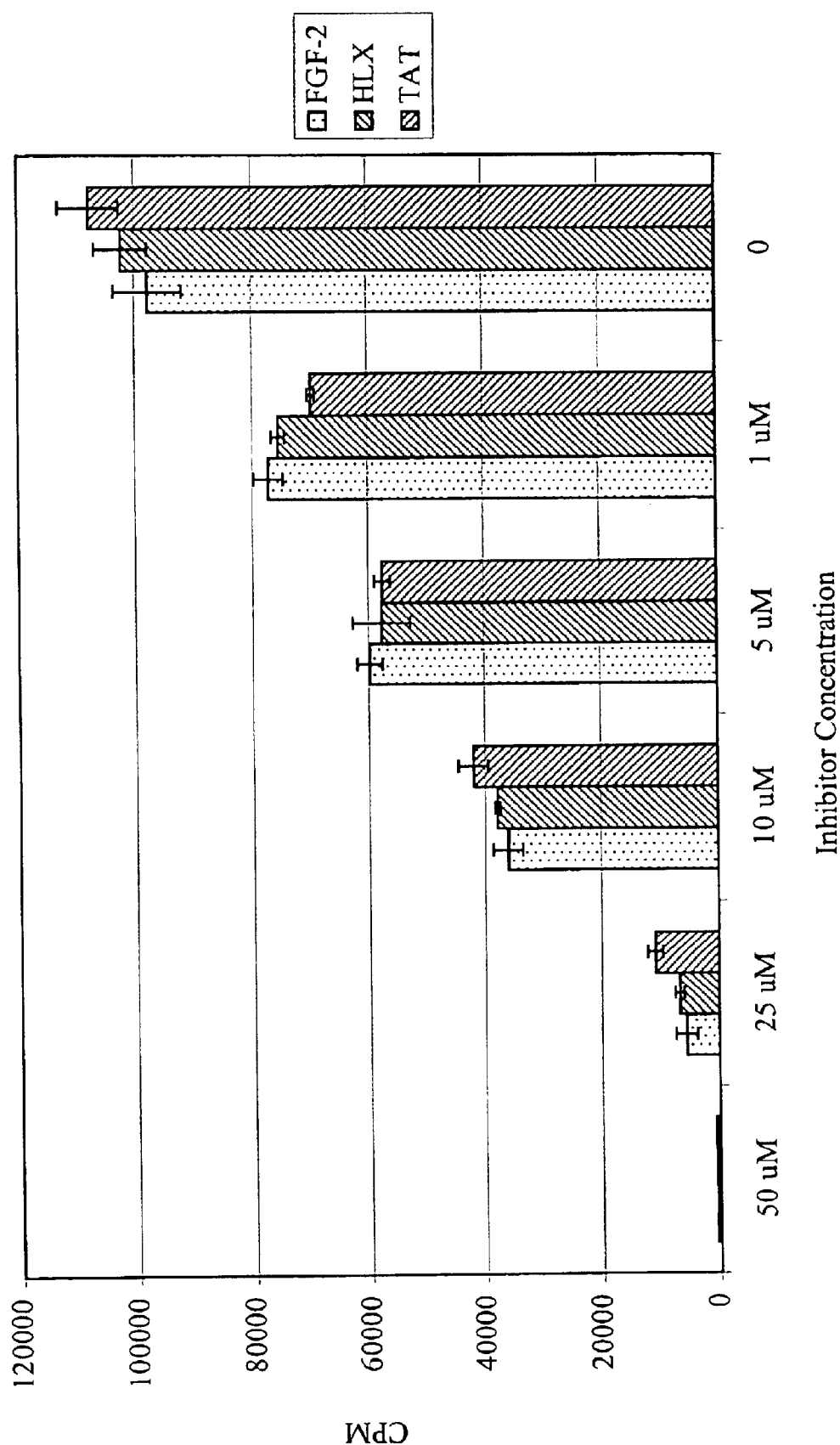
FIG. 8B is a graph demonstrating that treatment of cells with tyrosine kinase inhibitor Sugen SU4894 in the presence of wild type FGF-2, TAT-FGF-2, or HLX-FGF-2, effectively blocked DNA synthesis.

In this experiment, MM14 cells incubated in the presence or absence of FGF-2, TAT-FGF-2 or HLX-FGF-2 were treated with either tyrosine kinase inhibitor Tyrphostin AG1296 or Sugen SU4894. After 16 hrs, cells were subjected to cell cycle exit assays to assess for proliferation. FIGS. 8A and 8B show that treatment of MM14 cells with either inhibitor in the presence of wild type FGF-2, TAT-FGF-2, or HLX-FGF-2 effectively blocked DNA synthesis. These results strongly suggest that in addition to the FGF receptor requirement, phosphorylation of the receptor is also required to mediate the activity of the penetratin fusions. Unfortunately, it was not possible to directly demonstrate that the inhibitors block receptor phosphorylation, since the low number of FGF receptors on the MM14 cells (–700/cell) do not allow visualization of the receptor autophosphorylation as the present inventors have previously reported.

Example 10

The following example shows that chimeric FGF-2 appears to signal through the same intracellular molecules required for wild type FGF-2 signaling in MM14 cells.

The demonstration that receptor phosphorylation is required for HLX-FGF-2 and TATFGF-2 activity suggests that these factors use existing signaling pathways to repress terminal differentiation and promote proliferation via intracellular FGF receptors. To provide more conclusive evidence supporting this hypothesis, the activity of both HLX-FGF-2 and TAT-FGF-2 in the presence of specific MKK inhibitors was tested. A recent report from the present inventors' laboratory has demonstrated that the pathways mediating repression of myogenic differentiation and stimulation of cell proliferation diverge following activation of FGFR1. Proliferation requires activation of the raf/ERK1/2 pathway. Inhibitors of this pathway block proliferation of MM14 cells but do not affect differentiation in the presence of FGF-2.

Figure 8C:
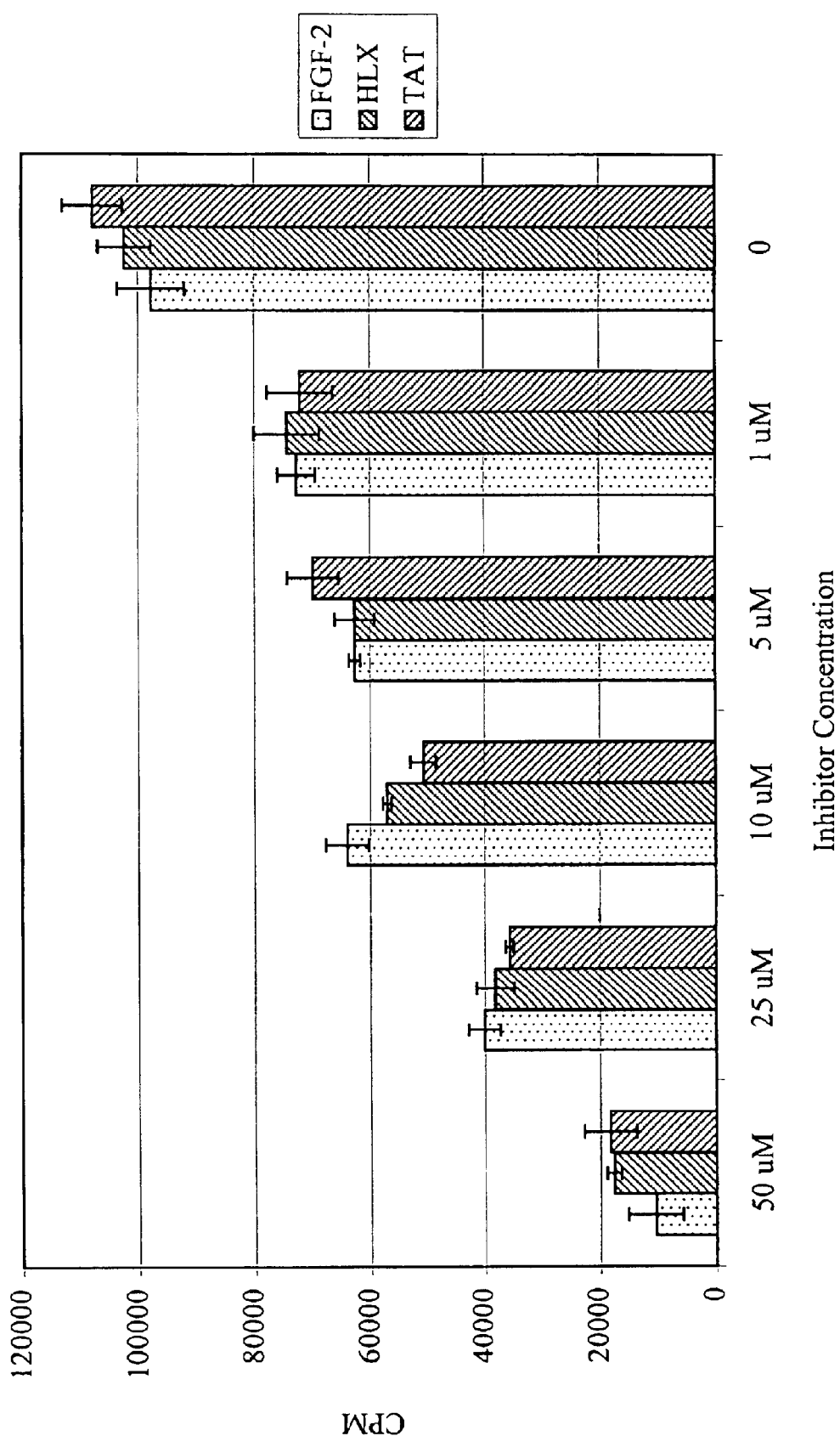
FIG. 8C is a graph demonstrating that treatment of MM14 cells with PD098059, a specific inhibitor of MKK1, blocked both wild type and penatratin-FGF-stimulated proliferation of the cells.
Figure 8D:
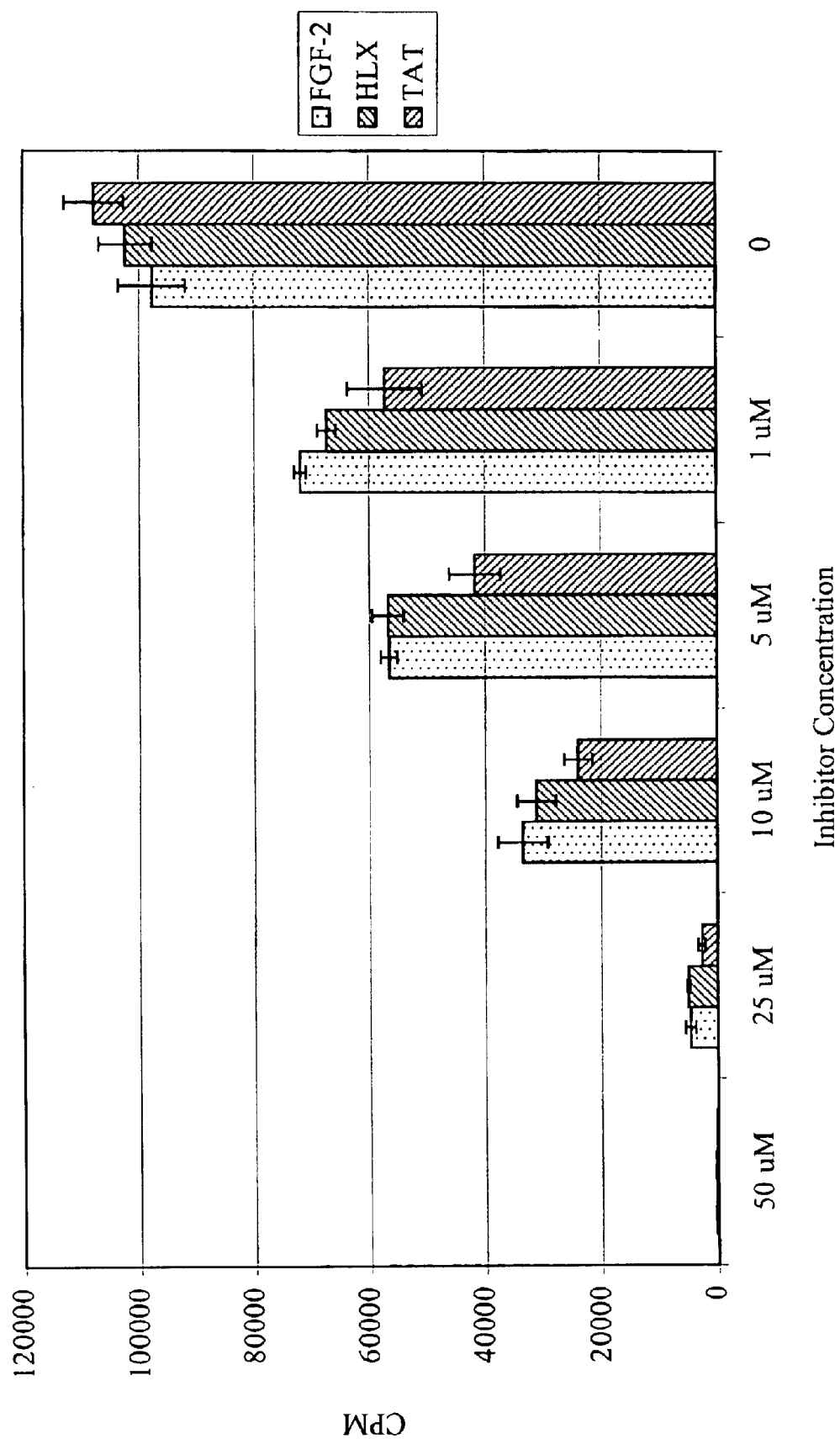
FIG. 8D is a graph demonstrating that treatment of MM14 cells with U0126, an inhibitor of both MKK1 and MKK2, blocked both wild type and penatratin-FGF-stimulated proliferation of the cells.

In this experiment, MM14 cells incubated in the presence or absence of FGF-2, TAT-FGF-2 or HLX-FGF-2 were treated with either the MKK1 inhibitor PD098059 or the MKK1 ½ inhibitor U0126. After 16 hrs, cells were subjected to cell cycle exit assays to assess for proliferation. Addition of either PD098059 (Dudley, et al.,(1995) *Proc Natl Acad Sci USA*, 92:7686–9), a specific inhibitor of MKK1 or U0126 (Favata, et al., (1998) *J Biol Chem*, 273:18623–32), an inhibitor of both MKK1 and MKK2, blocked wild type and penatratin-FGF-stimulated proliferation of MM14 cells (FIGS. 8C and 8D). Together, the observations in Examples 9 and 10 lead to the conclusion that the activity of intracellularly localized TAT-FGF-2 and HLX-FGF-2 requires stimulation of FGF receptors and subsequent activation of intracellular signaling pathways utilized by the wild type FGF signaling complex. Thus, activation of the raf/ERK pathway appears to be required for TAT-FGF-2 and HLX-FGF-2 function.

Without being bound by theory, the present inventors propose the following speculative model to explain the mechanism of action of the chimeric FGF proteins of the present invention. The data presented in Examples 1–10 suggests that FGF proteins act at an intracellular site and require functional FGFR1 to be present in order to transduce FGF-specific signals. These intracellular FGFs could be functioning by activating either newly synthesized or previously internalized FGFR1 and routing the receptors to an intracellular, perhaps perinuclear, site. It is suggested that the ligand-dependent routing of the receptor may be a critical aspect of proliferative signaling missing from the present inventors' previous chimeric FGF receptor studies (Kudla, et al., (1998) *J. Cell Biol.*, in press). Activation of these chimeric receptors, which contain the extracellular domain of the PDGF receptor and the intracellular domain of the FGF receptor, by the addition of PDGF-BB was shown to result in repression of differentiation, but failed to provide the signal(s) necessary for proliferation. These data, along with the data presented in this report are consistent with Prudovsky et al observations and support a model of FGF signaling which requires routing of the FGF ligand-receptor complex to an appropriate intracellular location in order to access requisite signaling substrates. This model does not suggest that these putative substrates acted on by the routed ligand-receptor complex are solely sufficient for the proliferative response, but rather necessary in addition to the raf/ERK mediated signals.

Since TAT-FGF-2 and HLX-FGF-2 do not exhibit an absolute requirement for heparan sulfate, it is proposed that the intracellularly localized FGFRI is not accompanied by heparan sulfate proteoglycans or the GAG chains. An inhibitory function for heparan sulfate has been recently proposed and if active only at the cell surface, these results could explain why the penetratin FGF-2 fusions are active at an intracellular site and not dependent on heparan sulfate. After crossing the plasma membrane, penetratin FGF-2 should be capable of accessing any intracellular membrane bound structure. By virtue of this property, penetratin FGF-2 could enter vesicular compartments that bear FGF receptors trafficking to or away from the plasma membrane. Upon entering these compartments, the penetratin FGF-2 could activate the receptor inside the cell. The relative insensitivity of penetratin FGF-2 to heparan sulfate would be likely to allow for intracellular activation of the receptor in either the presence or absence of heparan sulfate proteoglycans. Intracellular activation of the FGF receptor would then result in the activation of those pathways utilized by normal cell surface FGF signaling. Additionally, this receptor activation may also serve to route the receptor bearing vesicular compartments to the nucleus where the activated receptor may act on additional unidentified target molecules required for the full FGF mediated biological response.

However, this does not appear to be true for all FGFR1-stimulated intracellular signaling pathways. While the examples demonstrated that the intracellular action of the penetratin FGF-2 fusion proteins required activation of the raf/ERK pathway, these proteins were not inhibited by a dominant negative ras mutant ($Ras^{N17}$), which blocks activity of wildtype FGF-2. Alternatively, the penetratin fusion proteins could be acting on intracellular FGFR1 that has been translocated to a specific intracellular site.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A chimeric fibroblast growth factor-2 (FGF-2), comprising:
   a) a biologically active fibroblast growth factor-2 (FGF-2) protein having a first amino acid sequence that is encoded by a nucleic acid sequence that is at least about 90% identical to a nucleic acid sequence encoding a fibroblast growth factor-2 (FGF-2) protein represented by SEQ ID NO:5 or SEQ ID NO:6, wherein the FGF-2 protein has an FGF-2 biological activity selected from the group consisting of: promotion of cell proliferation, repression of terminal differentiation in a cell, promotion of angiogenesis, promotion of wound healing, promotion of osteogenesis, and promotion of nerve outgrowth; and,
   b) a penetratin peptide having a second amino acid sequence, wherein the penetratin peptide is selected from the group consisting of:
      i) a first peptide comprising an amino acid sequence selected from the group consisting of:
         1) $X_1$-$X_2$-$X_3$-$X_4$-$X_5$-$X_6$-$X_7$-$X_8$-$X9$-$X_{10}$-$X_{11}$-$X_{12}$-$X_{13}$-$X_{14}$-$X_{15}$-$X_{16}$; and,
         2) $X_{16}$-$X_{15}$-$X_{14}$-$X_{13}$-$X_{12}$-$X_{11}$-$X_{10}$-$X_9$-$X_8$-$X_7$-$X_6$-$X_5$-$X_4$-$X_3$-$X_2$-$X_1$;
         wherein $X_1$, $X_2$, $X_3$, $X_4$, $X_5$, $X_7$, $X_8$, $X_9$, $X_{10}$, $X_{11}$, $X_{12}$, $X_{13}$, $X_{14}$, $X_{15}$, and $X_{16}$ each represent an α-amino acid, between 6 and 10 of which are hydrophobic amino acids; and wherein $X_6$ represents Trp; and,
      ii) a second peptide comprising amino acid residues 49–57 of HIV Tat protein (SEQ ID NO:17).
   wherein the biological activity of said penetratin peptide is to transport said chimeric fibroblast growth factor-2 (FGF-2) across a lipid bilayer of a cell independently of the presence of an FGF-2 receptor;

wherein said second amino acid sequence is linked to said first amino acid sequence; and wherein said chimeric fibroblast growth factor-2 (FGF-2) is characterized by:

i) said FGF-2 biological activity of (a) in the absence of heparan sulfate; and, ii) entry into a living cell in the absence of a receptor that binds to FGF-2.

2. The chimeric fibroblast growth factor-2 (FGF-2) of claim 1, wherein said chimeric FGF-2 has biological activity that is characterized by:

a) repression of terminal differentiation in the absence of heparan sulfate; and, b) promotion of cell proliferation in the absence of heparan sulfate.

3. The chimeric fibroblast growth factor-2 (FGF-2) of claim 1, wherein said second amino acid sequence is linked to the N-terminus of said first amino acid sequence.

4. The chimeric fibroblast growth factor-2 (FGF-2) of claim 1, wherein said first amino acid sequence is selected from the group consisting of SEQ ID NO:5 and SEQ ID NO:6.

5. The chimeric fibroblast growth factor-2 (FGF-2) of claim 1, wherein said FGF-2 protein has an amino acid sequence comprising from position 18 through position 172 of SEQ ID NO:2 or from position 17 through 171 of SEQ ID NO:4.

6. The chimeric fibroblast growth factor-2 (FGF-2) of claim 1, wherein said second peptide does not comprise amino acid residues 22–36 or 73–86 of HIV Tat protein (SEQ ID NO:]17).

7. The chimeric fibroblast growth factor-2 (FGF-2) of claim 1, wherein said first peptide is selected from the group consisting of a peptide comprising helix 3 of a homeobox domain and a homeobox domain.

8. The chimeric fibroblast growth factor-2 (FGF-2) of claim 1, wherein said first peptide comprises an amino acid sequence selected from the group consisting of SEQ ID NO:9, amino acid residues 42 through 58 of SEQ ID NO:9, amino acid residues 43 through 59 of SEQ ID NO:9, amino acid residues 43 through 58 of SEQ ID NO:9, SEQ ID NO:10, SEQ ID NO:11, SEQ ID NO:12, SEQ ID NO:13, SEQ ID NO:14, SEQ ID NO:15, and SEQ ID NO:16.

9. The chimeric fibroblast growth factor-2 (FGF-2) of claim 1, wherein said first peptide comprises amino acid residues 2–17 of SEQ ID NO:2.

10. The chimeric fibroblast growth factor-2 (FGF-2) of claim 1, wherein said second peptide comprises an amino acid sequence from an HIV Tat protein selected from the group consisting of amino acid residues 37–72 of SEQ ID NO:17, amino acid residues 38–72 of SEQ ID NO:17, amino acid residues 47–72 of SEQ ID NO:17, amino acid residues 37–58 of SEQ ID NO:17, amino acid residues 38–58 of SEQ ID NO:17, amino acid residues 47–58 of SEQ ID NO:17, amino acid residues 1–21 and 38–72 of SEQ ID NO:17, amino acid residues 47–62 of SEQ ID NO:17, amino acid residues 38–62 of SEQ ID NO:17, amino acid residues 1–72 of SEQ ID NO:17, amino acid residues 1–58 of SEQ ID NO:17, and amino acid residues 48–60 of SEQ ID NO:17.

11. The chimeric fibroblast growth factor-2 (FGF-2) of claim 1, wherein said second peptide comprises amino acid residues 48–60 of SEQ ID NO:17 or amino acid residues 2–14 of SEQ ID NO:4.

12. The chimeric fibroblast growth factor-2 (FGF-2) of claim 1, wherein said chimeric fibroblast growth factor-2 (FGF-2) comprises an amino acid sequence selected from the group consisting of SEQ ID NO:2 (HLX-FGF) and SEQ ID NO:4 (TAT-FGF).

13. A therapeutic composition comprising the chimeric fibroblast growth factor-2 (FCF-2) of claim 1 and a pharmaceutically acceptable excipient.

14. The chimeric fibroblast growth factor-2 (FGF-2) of claim 1, wherein said first amino acid sequence is SEQ ID NO:5.

15. The chimeric fibroblast growth factor-2 (FGF-2) of claim 1, wherein said first amino acid sequence is SEQ ID NO:6.

* * * * *

SEQUENCE LISTING

<160> NUMBER OF SEQ ID NOS: 27

<210> SEQ ID NO 1
<211> LENGTH: 556
<212> TYPE: DNA
<213> ORGANISM: chimeric sequence
<220> FEATURE:
<221> NAME/KEY: CDS
<222> LOCATION: (8)..(553)

<400> SEQUENCE: 1

```
ggtagtc atg aga cag atc aag atc tgg ttt cag aac cgg cgc atg aag         49
        Met Arg Gln Ile Lys Ile Trp Phe Gln Asn Arg Arg Met Lys
          1               5                  10 tgg aaa aag gcg gct gct ggt tct atc act acc ctg cca gct ctg cca         97
Trp Lys Lys Ala Ala Ala Gly Ser Ile Thr Thr Leu Pro Ala Leu Pro
 15                  20                  25                  30 gaa gac ggt ggt tct ggt gcc ttc cca cca ggt cac ttc aaa gac cca        145
Glu Asp Gly Gly Ser Gly Ala Phe Pro Pro Gly His Phe Lys Asp Pro
                 35                  40                  45 aaa cgt ctg tac tgc aaa aac ggt ggt ttc ttc ctg cgc atc cac ccc        193
Lys Arg Leu Tyr Cys Lys Asn Gly Gly Phe Phe Leu Arg Ile His Pro
             50                  55                  60 gac ggc cga gtg gac ggg gtc cgc gag aag agc gac cca cac atc aaa        241
Asp Gly Arg Val Asp Gly Val Arg Glu Lys Ser Asp Pro His Ile Lys
 65                  70                  75 cta caa ctt caa gca gaa gag aga ggg gtt gtg tct atc aaa gga gtg        289
Leu Gln Leu Gln Ala Glu Glu Arg Gly Val Val Ser Ile Lys Gly Val
             80                  85                  90 tgt gca aac cgt tac ctt gct atg aaa gaa gat gga aga tta cta gct        337
Cys Ala Asn Arg Tyr Leu Ala Met Lys Glu Asp Gly Arg Leu Leu Ala
 95                 100                 105                 110 tct aaa tgt gtt aca gac gag tgt ttc ttt ttt gaa cga ttg gag tct        385
Ser Lys Cys Val Thr Asp Glu Cys Phe Phe Phe Glu Arg Leu Glu Ser
                115                 120                 125 aat aac tac aat act tac cgg tca agg aaa tac acc agt tgg tat gtg        433
Asn Asn Tyr Asn Thr Tyr Arg Ser Arg Lys Tyr Thr Ser Trp Tyr Val
            130                 135                 140 gca ctg aaa cga act ggg cag tat aaa ctt gga tcc aaa aca gga cct        481
Ala Leu Lys Arg Thr Gly Gln Tyr Lys Leu Gly Ser Lys Thr Gly Pro
145                 150                 155 ggg cag aaa gct ata ctt ttt ctt cca atg tct gct aag agc gaa cag        529
Gly Gln Lys Ala Ile Leu Phe Leu Pro Met Ser Ala Lys Ser Glu Gln
            160                 165                 170 aaa ctc atc tct gaa gag gat ctg tga                                    556
Lys Leu Ile Ser Glu Glu Asp Leu
175                 180
```

<210> SEQ ID NO 2
<211> LENGTH: 182
<212> TYPE: PRT
<213> ORGANISM: chimeric sequence

<400> SEQUENCE: 2

```
Met Arg Gln Ile Lys Ile Trp Phe Gln Asn Arg Arg Met Lys Trp Lys
  1               5                  10                  15

Lys Ala Ala Ala Gly Ser Ile Thr Thr Leu Pro Ala Leu Pro Glu Asp
                 20                  25                  30

Gly Gly Ser Gly Ala Phe Pro Pro Gly His Phe Lys Asp Pro Lys Arg
             35                  40                  45
```

```
Leu Tyr Cys Lys Asn Gly Gly Phe Phe Leu Arg Ile His Pro Asp Gly
 50                  55                  60

Arg Val Asp Gly Val Arg Glu Lys Ser Asp Pro His Ile Lys Leu Gln
 65                  70                  75                  80

Leu Gln Ala Glu Glu Arg Gly Val Val Ser Ile Lys Gly Val Cys Ala
                 85                  90                  95

Asn Arg Tyr Leu Ala Met Lys Glu Asp Gly Arg Leu Leu Ala Ser Lys
            100                 105                 110

Cys Val Thr Asp Glu Cys Phe Phe Glu Arg Leu Glu Ser Asn Asn
            115                 120                 125

Tyr Asn Thr Tyr Arg Ser Arg Lys Tyr Thr Ser Trp Tyr Val Ala Leu
            130                 135                 140

Lys Arg Thr Gly Gln Tyr Lys Leu Gly Ser Lys Thr Gly Pro Gly Gln
145                 150                 155                 160

Lys Ala Ile Leu Phe Leu Pro Met Ser Ala Lys Ser Glu Gln Lys Leu
                165                 170                 175

Ile Ser Glu Glu Asp Leu
            180

<210> SEQ ID NO 3
<211> LENGTH: 556
<212> TYPE: DNA
<213> ORGANISM: chimeric sequence
<220> FEATURE:
<221> NAME/KEY: CDS
<222> LOCATION: (11)..(553)

<400> SEQUENCE: 3
ggtagtccat atg ggc cgc aaa aaa cgc cgc cag cgc cgc cgc ccg ccg        49
           Met Gly Arg Lys Lys Arg Arg Gln Arg Arg Arg Pro Pro
            1               5                  10 cag gaa ttc gcg gct gct ggt tct atc act acc ctg cca gct ctg cca       97
Gln Glu Phe Ala Ala Ala Gly Ser Ile Thr Thr Leu Pro Ala Leu Pro
 15                  20                  25 gaa gac ggt ggt tct ggt gcc ttc cca cca ggt cac ttc aaa gac cca      145
Glu Asp Gly Gly Ser Gly Ala Phe Pro Pro Gly His Phe Lys Asp Pro
 30                  35                  40                  45 aaa cgt ctg tac tgc aaa aac ggt ggt ttc ttc ctg cgc atc cac ccc      193
Lys Arg Leu Tyr Cys Lys Asn Gly Gly Phe Phe Leu Arg Ile His Pro
             50                  55                  60 gac ggc cga gtg gac ggg gtc cgc gag aag agc gac cca cac atc aaa      241
Asp Gly Arg Val Asp Gly Val Arg Glu Lys Ser Asp Pro His Ile Lys
         65                  70                  75 cta caa ctt caa gca gaa gag aga ggg gtt gtg tct atc aaa gga gtg      289
Leu Gln Leu Gln Ala Glu Glu Arg Gly Val Val Ser Ile Lys Gly Val
     80                  85                  90 tgt gca aac cgt tac ctt gct atg aaa gaa gat gga aga tta cta gct      337
Cys Ala Asn Arg Tyr Leu Ala Met Lys Glu Asp Gly Arg Leu Leu Ala
 95                 100                 105 tct aaa tgt gtt aca gac gag tgt ttc ttt ttt gaa cga ttg gag tct      385
Ser Lys Cys Val Thr Asp Glu Cys Phe Phe Phe Glu Arg Leu Glu Ser
110                 115                 120                 125 aat aac tac aat act tac cgg tca agg aaa tac acc agt tgg tat gtg      433
Asn Asn Tyr Asn Thr Tyr Arg Ser Arg Lys Tyr Thr Ser Trp Tyr Val
            130                 135                 140 gca ctg aaa cga act ggg cag tat aaa ctt gga tcc aaa aca gga cct      481
Ala Leu Lys Arg Thr Gly Gln Tyr Lys Leu Gly Ser Lys Thr Gly Pro
            145                 150                 155
```

```
ggg cag aaa gct ata ctt ttt ctt cca atg tct gct aag agc gaa cag    529
Gly Gln Lys Ala Ile Leu Phe Leu Pro Met Ser Ala Lys Ser Glu Gln
        160             165                 170 aaa ctc atc tct gaa gag gat ctg tga                                556
Lys Leu Ile Ser Glu Glu Asp Leu
    175             180
```

<210> SEQ ID NO 4
<211> LENGTH: 181
<212> TYPE: PRT
<213> ORGANISM: chimeric sequence

<400> SEQUENCE: 4

```
Met Gly Arg Lys Lys Arg Arg Gln Arg Arg Arg Pro Pro Gln Glu Phe
 1               5                  10                  15

Ala Ala Ala Gly Ser Ile Thr Thr Leu Pro Ala Leu Pro Glu Asp Gly
            20                  25                  30

Gly Ser Gly Ala Phe Pro Pro Gly His Phe Lys Asp Pro Lys Arg Leu
        35                  40                  45

Tyr Cys Lys Asn Gly Gly Phe Phe Leu Arg Ile His Pro Asp Gly Arg
    50                  55                  60

Val Asp Gly Val Arg Glu Lys Ser Asp Pro His Ile Lys Leu Gln Leu
65                  70                  75                  80

Gln Ala Glu Glu Arg Gly Val Val Ser Ile Lys Gly Val Cys Ala Asn
                85                  90                  95

Arg Tyr Leu Ala Met Lys Glu Asp Gly Arg Leu Leu Ala Ser Lys Cys
            100                 105                 110

Val Thr Asp Glu Cys Phe Phe Phe Glu Arg Leu Glu Ser Asn Asn Tyr
        115                 120                 125

Asn Thr Tyr Arg Ser Arg Lys Tyr Thr Ser Trp Tyr Val Ala Leu Lys
    130                 135                 140

Arg Thr Gly Gln Tyr Lys Leu Gly Ser Lys Thr Gly Pro Gly Gln Lys
145                 150                 155                 160

Ala Ile Leu Phe Leu Pro Met Ser Ala Lys Ser Glu Gln Lys Leu Ile
                165                 170                 175

Ser Glu Glu Asp Leu
            180
```

<210> SEQ ID NO 5
<211> LENGTH: 146
<212> TYPE: PRT
<213> ORGANISM: Bos taurus

<400> SEQUENCE: 5

```
Pro Ala Leu Pro Glu Asp Gly Gly Ser Gly Ala Phe Pro Pro Gly His
 1               5                  10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95
```

-continued

Arg Leu Glu Ser Asn Asn Tyr Asn Thr Tyr Arg Ser Arg Lys Tyr Ser
                100                 105                 110

Ser Trp Tyr Val Ala Leu Lys Arg Thr Gly Gln Tyr Lys Leu Gly Pro
            115                 120                 125

Lys Thr Gly Pro Gly Gln Lys Ala Ile Leu Phe Leu Pro Met Ser Ala
        130                 135                 140

Lys Ser
145

<210> SEQ ID NO 6
<211> LENGTH: 146
<212> TYPE: PRT
<213> ORGANISM: Homo sapiens

<400> SEQUENCE: 6

Pro Ala Leu Pro Glu Asp Gly Gly Ser Gly Ala Phe Pro Pro Gly His
 1               5                  10                  15

Phe Lys Asp Pro Lys Arg Leu Tyr Cys Lys Asn Gly Gly Phe Phe Leu
                20                  25                  30

Arg Ile His Pro Asp Gly Arg Val Asp Gly Val Arg Glu Lys Ser Asp
            35                  40                  45

Pro His Ile Lys Leu Gln Leu Gln Ala Glu Glu Arg Gly Val Val Ser
        50                  55                  60

Ile Lys Gly Val Cys Ala Asn Arg Tyr Leu Ala Met Lys Glu Asp Gly
 65                 70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Thr
                100                 105                 110

Ser Trp Tyr Val Ala Leu Lys Arg Thr Gly Gln Tyr Lys Leu Gly Ser
            115                 120                 125

Lys Thr Gly Pro Gly Gln Lys Ala Ile Leu Phe Leu Pro Met Ser Ala
        130                 135                 140

Lys Ser
145

<210> SEQ ID NO 7
<211> LENGTH: 140
<212> TYPE: PRT
<213> ORGANISM: Bos taurus

<400> SEQUENCE: 7

Phe Asn Leu Pro Leu Gly Asn Tyr Lys Lys Pro Lys Leu Leu Tyr Cys
 1               5                  10                  15

Ser Asn Gly Gly Tyr Phe Leu Arg Ile Leu Pro Asp Gly Thr Val Asp
                20                  25                  30

Gly Thr Lys Asp Arg Ser Asp Gly His Ile Gln Leu Phe Leu Cys Ala
            35                  40                  45

Glu Ser Ile Gly Glu Val Tyr Ile Lys Ser Thr Glu Thr Gly Gln Phe
        50                  55                  60

Leu Ala Met Asp Thr Asp Gly Leu Leu Tyr Gly Ser Gln Thr Pro Asp
 65                 70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys His Trp Phe Val Gly Leu Lys
                100                 105                 110

```
Lys Asn Gly Arg Ser Lys Leu Glu Pro Arg Thr His Phe Gly Gln Lys
        115                 120                 125

Ala Ile Leu Phe Leu Pro Leu Pro Val Ser Ser Asp
130                 135                 140

<210> SEQ ID NO 8
<211> LENGTH: 140
<212> TYPE: PRT
<213> ORGANISM: Homo sapiens

<400> SEQUENCE: 8

Phe Asn Leu Pro Pro Gly Asn Tyr Lys Lys Pro Lys Leu Leu Tyr Cys
  1               5                  10                  15

Ser Asn Gly Gly His Phe Leu Arg Ile Leu Pro Asp Gly Thr Tyr Asp
             20                  25                  30

Gly Thr Arg Asp Arg Ser Asp Gln His Ile Gln Leu Gln Leu Ser Ala
         35                  40                  45

Glu Ser Tyr Gly Glu Tyr Ile Lys Ser Thr Glu Thr Gly Gln Tyr
 50                  55                  60

Leu Ala Met Asp Thr Asp Gly Leu Leu Tyr Gly Ser Gln Thr Pro Asn
 65                  70                  75                  80

Glu Glu Cys Leu Phe Leu Glu Arg Leu Glu Asn His Tyr Asn Thr
                 85                  90                  95

Tyr Ile Ser Lys Lys His Ala Glu Lys Asn Trp Phe Tyr Gly Leu Lys
                100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Tyr Ser Ser Asp
130                 135                 140

<210> SEQ ID NO 9
<211> LENGTH: 60
<212> TYPE: PRT
<213> ORGANISM: Drosophila sp.

<400> SEQUENCE: 9

Arg Lys Arg Gly Arg Glu Thr Tyr Thr Arg Tyr Gln Thr Leu Glu Leu
  1               5                  10                  15

Glu Lys Glu Phe His Phe Asn Arg Tyr Leu Thr Arg Arg Arg Arg Ile
             20                  25                  30

Glu Ile Ala His Ala Leu Cys Leu Thr Glu Arg Gln Ile Lys Ile Trp
         35                  40                  45

Phe Gln Asn Arg Arg Met Lys Trp Lys Lys Glu Asn
 50                  55                  60

<210> SEQ ID NO 10
<211> LENGTH: 60
<212> TYPE: PRT
<213> ORGANISM: Drosophila sp.

<400> SEQUENCE: 10

Arg Lys Arg Gly Arg Gln Thr Tyr Thr Arg Tyr Gln Thr Leu Glu Leu
  1               5                  10                  15

Glu Lys Glu Phe His Phe Asn Arg Tyr Leu Thr Arg Arg Arg Arg Ile
             20                  25                  30
```

```
Glu Ile Ala Tyr Ala Leu Cys Leu Thr Gln Arg Gln Ile Lys Ile Trp
            35                  40                  45

Phe Ala Asn Arg Arg Met Lys Trp Lys Lys Glu Asn
50                  55                  60

<210> SEQ ID NO 11
<211> LENGTH: 60
<212> TYPE: PRT
<213> ORGANISM: Drosophila sp.

<400> SEQUENCE: 11

Arg Lys Arg Gly Arg Gln Thr Tyr Thr Arg Tyr Gln Thr Leu Glu Leu
1               5                   10                  15

Glu Lys Glu Phe His Phe Asn Arg Tyr Leu Thr Arg Arg Arg Arg Ile
            20                  25                  30

Glu Ile Ala His Ala Leu Cys Pro Pro Glu Arg Gln Ile Lys Ile Trp
            35                  40                  45

Phe Gln Asn Arg Arg Met Lys Trp Lys Lys Glu Asn
50                  55                  60

<210> SEQ ID NO 12
<211> LENGTH: 16
<212> TYPE: PRT
<213> ORGANISM: Drosophila sp.

<400> SEQUENCE: 12

Arg Gln Ile Lys Ile Trp Phe Pro Asn Arg Arg Met Lys Trp Lys Lys
1               5                   10                  15

<210> SEQ ID NO 13
<211> LENGTH: 16
<212> TYPE: PRT
<213> ORGANISM: Drosophila sp.

<400> SEQUENCE: 13

Arg Gln Pro Lys Ile Trp Phe Pro Asn Arg Arg Lys Pro Trp Lys Lys
1               5                   10                  15

<210> SEQ ID NO 14
<211> LENGTH: 16
<212> TYPE: PRT
<213> ORGANISM: Drosophila sp.

<400> SEQUENCE: 14

Arg Gln Ile Lys Ile Trp Phe Gln Asn Met Arg Lys Trp Lys Lys
1               5                   10                  15

<210> SEQ ID NO 15
<211> LENGTH: 16
<212> TYPE: PRT
<213> ORGANISM: Drosophila sp.

<400> SEQUENCE: 15

Arg Gln Ile Lys Ile Trp Phe Gln Asn Arg Arg Met Arg Trp Arg Arg
1               5                   10                  15

<210> SEQ ID NO 16
<211> LENGTH: 16
<212> TYPE: PRT
<213> ORGANISM: Drosophila sp.
```

```
<400> SEQUENCE: 16

Arg Arg Trp Arg Arg Trp Trp Arg Arg Trp Trp Arg Arg Trp Arg Arg
 1               5                  10                  15

<210> SEQ ID NO 17
<211> LENGTH: 86
<212> TYPE: PRT
<213> ORGANISM: Human immunodeficiency virus

<400> SEQUENCE: 17

Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
             20                  25                  30

His Cys Gln Val Cys Phe Ile Thr Lys Ala Leu Gly Ile Ser Tyr Gly
         35                  40                  45

Arg Lys Lys Arg Arg Gln Arg Arg Pro Pro Gln Gly Ser Gln Thr
     50                  55                  60

His Gln Val Ser Leu Ser Lys Gln Pro Thr Ser Gln Ser Arg Gly Asp
 65                  70                  75                  80

Pro Thr Gly Pro Lys Glu
                 85

<210> SEQ ID NO 18
<211> LENGTH: 60
<212> TYPE: DNA
<213> ORGANISM: primer
<220> FEATURE:
<221> NAME/KEY: CDS
<222> LOCATION: (1)..(48)

<400> SEQUENCE: 18 cca atg tct gct aag agc gaa cag aaa ctc atc tct gaa gag gat ctg      48
Pro Met Ser Ala Lys Ser Glu Gln Lys Leu Ile Ser Glu Glu Asp Leu
 1               5                  10                  15 tgaaagcttg gg                                                        60

<210> SEQ ID NO 19
<211> LENGTH: 16
<212> TYPE: PRT
<213> ORGANISM: primer

<400> SEQUENCE: 19

Pro Met Ser Ala Lys Ser Glu Gln Lys Leu Ile Ser Glu Glu Asp Leu
 1               5                  10                  15

<210> SEQ ID NO 20
<211> LENGTH: 60
<212> TYPE: DNA
<213> ORGANISM: primer

<400> SEQUENCE: 20
cccaagcttt cacagatcct cttcagagat gagttttcg ctgctcttag cagacattgg    60

<210> SEQ ID NO 21
<211> LENGTH: 59
<212> TYPE: DNA
<213> ORGANISM: primer
<220> FEATURE:
<221> NAME/KEY: CDS
<222> LOCATION: (11)..(58)
```

```
<400> SEQUENCE: 21
ggtagtccat atg ggc cgc aaa aaa cgc cgc cag cgc cgc cgc ccg ccg    49
           Met Gly Arg Lys Lys Arg Arg Gln Arg Arg Arg Pro Pro
            1               5                  10 cag gaa ttc c                                                     59
Gln Glu Phe
     15

<210> SEQ ID NO 22
<211> LENGTH: 16
<212> TYPE: PRT
<213> ORGANISM: primer

<400> SEQUENCE: 22

Met Gly Arg Lys Lys Arg Arg Gln Arg Arg Arg Pro Pro Gln Glu Phe
 1               5                  10                  15

<210> SEQ ID NO 23
<211> LENGTH: 16
<212> TYPE: DNA
<213> ORGANISM: primer

<400> SEQUENCE: 23
ggaattcctg cggcgg                                                 16

<210> SEQ ID NO 24
<211> LENGTH: 25
<212> TYPE: DNA
<213> ORGANISM: primer
<220> FEATURE:
<221> NAME/KEY: CDS
<222> LOCATION: (2)..(25)

<400> SEQUENCE: 24 g gaa ttc gcg gct gct ggt tct atc                                 25
  Glu Phe Ala Ala Ala Gly Ser Ile
   1               5

<210> SEQ ID NO 25
<211> LENGTH: 8
<212> TYPE: PRT
<213> ORGANISM: primer

<400> SEQUENCE: 25

Glu Phe Ala Ala Ala Gly Ser Ile
 1               5

<210> SEQ ID NO 26
<211> LENGTH: 81
<212> TYPE: DNA
<213> ORGANISM: primer
<220> FEATURE:
<221> NAME/KEY: CDS
<222> LOCATION: (11)..(79)

<400> SEQUENCE: 26
ggtagtccat atg aga cag atc aag atc tgg ttt cag aac cgg cgc atg    49
           Met Arg Gln Ile Lys Ile Trp Phe Gln Asn Arg Arg Met
            1               5                  10 aag tgg aaa aag gcg gct gct ggt tct atc ac                        81
Lys Trp Lys Lys Ala Ala Ala Gly Ser Ile
 15                  20
```

```
<210> SEQ ID NO 27
<211> LENGTH: 23
<212> TYPE: PRT
<213> ORGANISM: primer

<400> SEQUENCE: 27

Met Arg Gln Ile Lys Ile Trp Phe Gln Asn Arg Arg Met Lys Trp Lys
 1               5                  10                  15

Lys Ala Ala Ala Gly Ser Ile
            20
```